US012559575B2

(12) United States Patent
Tsimikas et al.

(10) Patent No.: US 12,559,575 B2
(45) Date of Patent: Feb. 24, 2026

(54) ISOFORM-INDEPENDENT ANTIBODIES TO LIPOPROTEIN(A)

(71) Applicant: The Regents of the University of California, Oakland, CA (US)

(72) Inventors: Sotirios Tsimikas, Rancho Santa Fe, CA (US); Joseph L. Witztum, San Diego, CA (US); Ayelet Gonen, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 680 days.

(21) Appl. No.: 17/921,621

(22) PCT Filed: Apr. 27, 2021

(86) PCT No.: PCT/US2021/029307

§ 371 (c)(1),
(2) Date: Oct. 26, 2022

(87) PCT Pub. No.: WO2021/222181

PCT Pub. Date: Nov. 4, 2021

(65) Prior Publication Data

US 2023/0167198 A1 Jun. 1, 2023

Related U.S. Application Data

(60) Provisional application No. 63/016,017, filed on Apr. 27, 2020.

(51) Int. Cl.

| | |
|---|---|
| ***C07K 16/00*** | (2006.01) |
| ***A61P 9/00*** | (2006.01) |
| ***C07K 16/44*** | (2006.01) |
| ***C12N 15/63*** | (2006.01) |

(52) U.S. Cl.

CPC ................ *C07K 16/44* (2013.01); *A61P 9/00* (2018.01); *C12N 15/63* (2013.01); *C07K 2317/565* (2013.01); *C07K 2317/622* (2013.01)

(58) Field of Classification Search

CPC ............. C07K 16/44; C07K 2317/565; C07K 2317/622; A61P 9/00; C12N 15/63

See application file for complete search history.

(56) References Cited

U.S. PATENT DOCUMENTS 5,486,476 A 1/1996 Burns et al.

FOREIGN PATENT DOCUMENTS

| | | | |
|---|---|---|---|
| JP | 6-279494 | A | 10/1994 |
| WO | 2011/121453 | A2 | 10/2011 |
| WO | 2011/151076 | A2 | 12/2011 |
| WO | 2020/010024 | A1 | 1/2020 |
| WO | 2022/076459 | A1 | 4/2022 |

OTHER PUBLICATIONS

Leibundgut et al (J Lipid Res 54:2815-2830, 2013) (Year: 2013).*
Tang, Xiaofan, International Preliminary Report on Patentability and Written Opinion, The International Bureau of WIPO, PCT/US2020/029307, Nov. 10, 2022.
Brouns, Gaby, Extended European Search Report, Application No. 21795836.2, European Patent Office, Apr. 12, 2024.
Marcovina, et al., "Effect of the Number of Apolipoprotein(a) Kringle 4 Domains on Immunochemical Measurements of Lipoprotein(a)", Clin. Chem., Feb. 1, 1995, vol. 41, No. 2, pp. 246-255.
Genbank Accession AAK52792.1, "Immunoglobulin kapa chain variable region, partial [Mus musculus]", Jul. 21, 2016, <URL:https://www.ncbi.nlm.nih.gov/protein/AAK52792.1>.
Genbank Accession OPZ71370.1, "Lipopolysaccharide core heptosyltransferase RfaQ [bacterium ADurb.Bin478]", Mar. 22, 2017, <URL:https://www.ncbi.nlm.nih.gov/protein/OPZ71370.1>.
Gonen et al., "Generation and characterization of LPA-KIV9, a murine monclonal antibody binding a single site on apolipoprotein(a)," J. Lipid Res., 61(9):1263-1270, Sep. 2020.
Shane, Thomas, International Search Report & Written Opinion, United States Patent & Trademark Office, PCT/US2020/029307, Oct. 21, 2021.
Nishi, Kenji, Office Action, Japan Patent Office, Application No. 2022-559805, Mar. 17, 2025.

* cited by examiner

*Primary Examiner* — Lei Yao
(74) *Attorney, Agent, or Firm* — Gavrilovich, Dodd & Lindsey LLP

(57) ABSTRACT

The disclosure provides for antibody and antibody fragments that bind to lipoprotein(a) epitopes and methods of use thereof, including the production of transgenic animal models and the use of the fragments as therapeutic and diagnostic agents for treating diseases and disorders associated with Lp(a).

17 Claims, 7 Drawing Sheets

Specification includes a Sequence Listing.

Epitope mapping using a printed peptide microarray

CRNPDSGKQPWCYTTDPCVRWEYCNLTQCSETESGVLETPTVVPVPSMEAHSEAAPTEQTPVVRQCYHGNGQSYRGTFS
TTVTGRTCQSWSSMTPHRHQRTPENYPNDGLTMNY

29 CSETESGVLETPTVV

30 SETESGVLETPTVVP

31 ETESGVLETPTVVPV

32 TESGVLETPTVVPVP

33 ESGVLETPTVVPVPS

34 SGVLETPTVVPVPSM

35 GVLETPTVVPVPSME

36 VLETPTVVPVPSMEA

37 LETPTVVPVPSMEAH

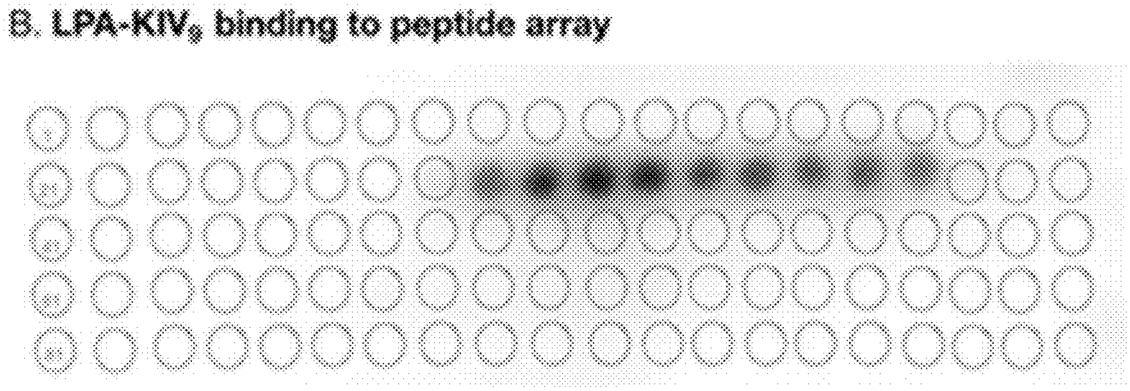
FIG. 4B
CSETESGVLETPTVVPVPSMEAH
FIG. 4C
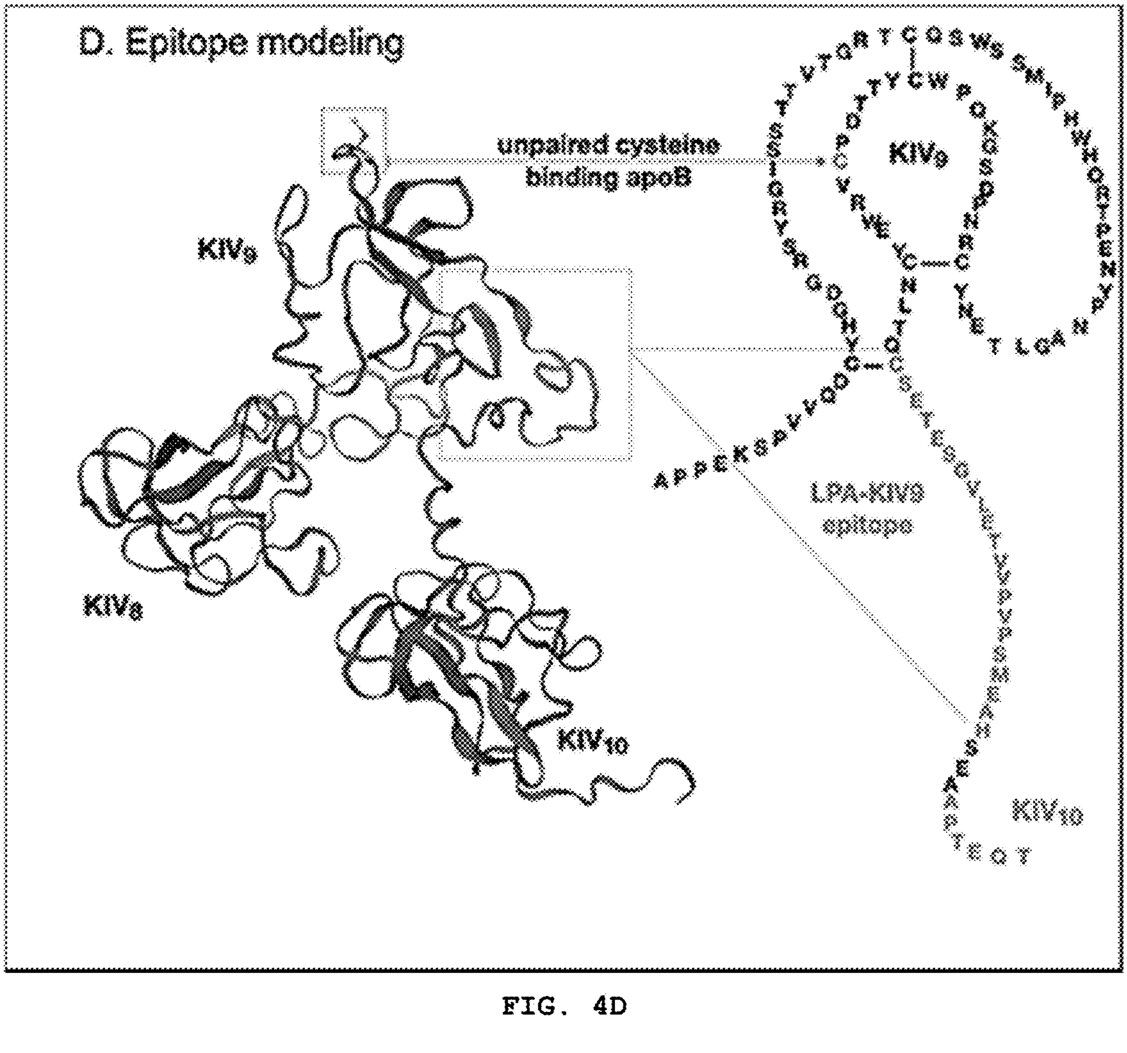
FIG. 4D

SEQUENCE LISTING

```
<160> NUMBER OF SEQ ID NOS: 34

<210> SEQ ID NO 1
<211> LENGTH: 399
<212> TYPE: DNA
<213> ORGANISM: Artificial Sequence
<220> FEATURE:
<223> OTHER INFORMATION: LPA-KIV9 Heavy chain
<220> FEATURE:
<221> NAME/KEY: CDS
<222> LOCATION: (1)..(399)

<400> SEQUENCE: 1

atg gaa tgg agc tgg gtc ttt ctc ttc ctc ctg tca gta act gca ggt       48
Met Glu Trp Ser Trp Val Phe Leu Phe Leu Leu Ser Val Thr Ala Gly
1               5                   10                  15

gtc caa tcc cag gtt caa ttg cag cag tct ggg gct gag ctg gtg agg       96
Val Gln Ser Gln Val Gln Leu Gln Gln Ser Gly Ala Glu Leu Val Arg
            20                  25                  30

cct ggg gct tca gtg aaa ctg tcc tgc aag gct ttg ggc tac aca ttt      144
Pro Gly Ala Ser Val Lys Leu Ser Cys Lys Ala Leu Gly Tyr Thr Phe
        35                  40                  45

act gac tat gaa ttg cac tgg ctg aag cag aca cct gtg cat ggc ctg      192
Thr Asp Tyr Glu Leu His Trp Leu Lys Gln Thr Pro Val His Gly Leu
    50                  55                  60

gaa tgg att gga gct gtt cat cca gga agc ggt ggt tct gcc tac aat      240
Glu Trp Ile Gly Ala Val His Pro Gly Ser Gly Gly Ser Ala Tyr Asn
65                  70                  75                  80

cag aac ttc aag gac aag gcc aca ctg act gca gac aaa tcc tcc agc      288
Gln Asn Phe Lys Asp Lys Ala Thr Leu Thr Ala Asp Lys Ser Ser Ser
                85                  90                  95

aca gcc tat atg gag ctc agc agc ctg aca tct gag gac tct gct gtc      336
Thr Ala Tyr Met Glu Leu Ser Ser Leu Thr Ser Glu Asp Ser Ala Val
            100                 105                 110
```

-continued

```
tat tac tgt aca aga gaa gga cct ttc tac tgg ggc caa ggc acc act      384
Tyr Tyr Cys Thr Arg Glu Gly Pro Phe Tyr Trp Gly Gln Gly Thr Thr
        115                 120                 125

ctc aca gtc tcc tca                                                  399
Leu Thr Val Ser Ser
    130


<210> SEQ ID NO 2
<211> LENGTH: 133
<212> TYPE: PRT
<213> ORGANISM: Artificial Sequence
<220> FEATURE:
<223> OTHER INFORMATION: Synthetic Construct

<400> SEQUENCE: 2

Met Glu Trp Ser Trp Val Phe Leu Phe Leu Leu Ser Val Thr Ala Gly
1               5                   10                  15

Val Gln Ser Gln Val Gln Leu Gln Gln Ser Gly Ala Glu Leu Val Arg
            20                  25                  30

Pro Gly Ala Ser Val Lys Leu Ser Cys Lys Ala Leu Gly Tyr Thr Phe
        35                  40                  45

Thr Asp Tyr Glu Leu His Trp Leu Lys Gln Thr Pro Val His Gly Leu
    50                  55                  60

Glu Trp Ile Gly Ala Val His Pro Gly Ser Gly Gly Ser Ala Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Glu Leu Ser Ser Leu Thr Ser Glu Asp Ser Ala Val
            100                 105                 110

Tyr Tyr Cys Thr Arg Glu Gly Pro Phe Tyr Trp Gly Gln Gly Thr Thr
        115                 120                 125

Leu Thr Val Ser Ser
    130


<210> SEQ ID NO 3
<211> LENGTH: 24
<212> TYPE: DNA
<213> ORGANISM: Artificial Sequence
<220> FEATURE:
<223> OTHER INFORMATION: LPA-KIV9 Heavy chain CDR1 coding sequence
<220> FEATURE:
<221> NAME/KEY: CDS
<222> LOCATION: (1)..(24)

<400> SEQUENCE: 3

ggc tac aca ttt act gac tat gaa                                       24
Gly Tyr Thr Phe Thr Asp Tyr Glu
1               5


<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Gly Tyr Thr Phe Thr Asp Tyr Glu
1               5


<210> SEQ ID NO 5
<211> LENGTH: 24
```

-continued

<212> TYPE: DNA
<213> ORGANISM: Artificial Sequence
<220> FEATURE:
<223> OTHER INFORMATION: LPA-KIV9 Heavy chain CDR2 coding sequence
<220> FEATURE:
<221> NAME/KEY: CDS
<222> LOCATION: (1)..(24)

<400> SEQUENCE: 5

```
gtt cat cca gga agc ggt ggt tct                                  24
Val His Pro Gly Ser Gly Gly Ser
1               5
```

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

```
Val His Pro Gly Ser Gly Gly Ser
1               5
```

<210> SEQ ID NO 7
<211> LENGTH: 27
<212> TYPE: DNA
<213> ORGANISM: Artificial Sequence
<220> FEATURE:
<223> OTHER INFORMATION: LPA-KIV9 Heavy chain CDR3 coding sequence
<220> FEATURE:
<221> NAME/KEY: CDS
<222> LOCATION: (1)..(27)

<400> SEQUENCE: 7

```
tgt aca aga gaa gga cct ttc tac tgg                              27
Cys Thr Arg Glu Gly Pro Phe Tyr Trp
1               5
```

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

```
Cys Thr Arg Glu Gly Pro Phe Tyr Trp
1               5
```

<210> SEQ ID NO 9
<211> LENGTH: 393
<212> TYPE: DNA
<213> ORGANISM: Artificial Sequence
<220> FEATURE:
<223> OTHER INFORMATION: LPA-KIV9 Light chain
<220> FEATURE:
<221> NAME/KEY: CDS
<222> LOCATION: (1)..(393)

<400> SEQUENCE: 9

```
atg aag ttg cct gtt agg ctg ttg gtg ctg atg ttc tgg att cct gct       48
Met Lys Leu Pro Val Arg Leu Leu Val Leu Met Phe Trp Ile Pro Ala
1               5                   10                  15

tcc agt agt gat gtt gtg atg acc caa act cca ctc tcc ctg cct gtc       96
Ser Ser Ser Asp Val Val Met Thr Gln Thr Pro Leu Ser Leu Pro Val
            20                  25                  30

agt ctt gga gat caa gcc tcc atc tct tgt aga tct agt cag agc ctt      144
```

-continued

```
Ser Leu Gly Asp Gln Ala Ser Ile Ser Cys Arg Ser Ser Gln Ser Leu
        35                  40                  45

gta cac agt aat gga aac gcc tat tta cat tgg tac ctg cag aag cca      192
Val His Ser Asn Gly Asn Ala Tyr Leu His Trp Tyr Leu Gln Lys Pro
    50                  55                  60

ggc cag tct cca aag ctc ctg atc tac aaa gtt tcc aac cga ttt tct      240
Gly Gln Ser Pro Lys Leu Leu Ile Tyr Lys Val Ser Asn Arg Phe Ser
65                  70                  75                  80

ggg gtc cca gac agg ttc agt ggc agt gga tca ggg aca aat ttc aca      288
Gly Val Pro Asp Arg Phe Ser Gly Ser Gly Ser Gly Thr Asn Phe Thr
                85                  90                  95

ctc aag atc agt aga gtg gag gct gag gat ctg gga att tat ttc tgc      336
Leu Lys Ile Ser Arg Val Glu Ala Glu Asp Leu Gly Ile Tyr Phe Cys
            100                 105                 110

tct caa agt aca cat gtt ccg ctc acg ttc ggt gct ggg acc aag ctg      384
Ser Gln Ser Thr His Val Pro Leu Thr Phe Gly Ala Gly Thr Lys Leu
        115                 120                 125

gag ctg aaa                                                          393
Glu Leu Lys
    130


<210> SEQ ID NO 10
<211> LENGTH: 131
<212> TYPE: PRT
<213> ORGANISM: Artificial Sequence
<220> FEATURE:
<223> OTHER INFORMATION: Synthetic Construct

<400> SEQUENCE: 10

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Ala Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asn Phe Thr
                85                  90                  95

Leu Lys Ile Ser Arg Val Glu Ala Glu Asp Leu Gly Ile Tyr Phe Cys
            100                 105                 110

Ser Gln Ser Thr His Val Pro Leu Thr Phe Gly Ala Gly Thr Lys Leu
        115                 120                 125

Glu Leu Lys
    130


<210> SEQ ID NO 11
<211> LENGTH: 33
<212> TYPE: DNA
<213> ORGANISM: Artificial Sequence
<220> FEATURE:
<223> OTHER INFORMATION: LPA-KIV9 Light chain CDR1 coding sequence
<220> FEATURE:
<221> NAME/KEY: CDS
<222> LOCATION: (1)..(33)

<400> SEQUENCE: 11

cag agc ctt gta cac agt aat gga aac gcc tat                           33
Gln Ser Leu Val His Ser Asn Gly Asn Ala Tyr
```

-continued

```
1               5                   10


<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Gln Ser Leu Val His Ser Asn Gly Asn Ala Tyr
1               5                   10


<210> SEQ ID NO 13
<211> LENGTH: 9
<212> TYPE: DNA
<213> ORGANISM: Artificial Sequence
<220> FEATURE:
<223> OTHER INFORMATION: LPA-KIV9 Light chain CDR2 coding sequence
<220> FEATURE:
<221> NAME/KEY: CDS
<222> LOCATION: (1)..(9)

<400> SEQUENCE: 13

aaa gtt tcc                                                            9
Lys Val Ser
1


<210> SEQ ID NO 14
<211> LENGTH: 33
<212> TYPE: DNA
<213> ORGANISM: Artificial Sequence
<220> FEATURE:
<223> OTHER INFORMATION: LPA-KIV9 Light chain CDR3 coding sequence
<220> FEATURE:
<221> NAME/KEY: CDS
<222> LOCATION: (1)..(33)

<400> SEQUENCE: 14

tgc tct caa agt aca cat gtt ccg ctc acg ttc                           33
Cys Ser Gln Ser Thr His Val Pro Leu Thr Phe
1               5                   10


<210> SEQ ID NO 15
<211> LENGTH: 11
<212> TYPE: PRT
<213> ORGANISM: Artificial Sequence
<220> FEATURE:
<223> OTHER INFORMATION: Synthetic Construct

<400> SEQUENCE: 15

Cys Ser Gln Ser Thr His Val Pro Leu Thr Phe
1               5                   10


<210> SEQ ID NO 16
<211> LENGTH: 4
<212> TYPE: PRT
<213> ORGANISM: Artificial Sequence
<220> FEATURE:
<223> OTHER INFORMATION: Peptide Linker

<400> SEQUENCE: 16

Gly Gly Gly Ser
1


<210> SEQ ID NO 17
<211> LENGTH: 7
<212> TYPE: PRT
```

<213> ORGANISM: Artificial Sequence
<220> FEATURE:
<223> OTHER INFORMATION: Lp(a) antigenic peptide

<400> SEQUENCE: 17

Leu Glu Thr Pro Thr Val Val
1 5

<210> SEQ ID NO 18
<211> LENGTH: 23
<212> TYPE: PRT
<213> ORGANISM: Artificial Sequence
<220> FEATURE:
<223> OTHER INFORMATION: Lp(a) antigenic peptide

<400> SEQUENCE: 18

Cys Ser Glu Thr Glu Ser Gly Val Leu Glu Thr Pro Thr Val Val Pro
1 5 10 15

Val Pro Ser Met Glu Ala His
20

<210> SEQ ID NO 19
<211> LENGTH: 2040
<212> TYPE: PRT
<213> ORGANISM: Homo sapiens

<400> SEQUENCE: 19

Met Glu His Lys Glu Val Val Leu Leu Leu Leu Leu Phe Leu Lys Ser
1 5 10 15

Ala Ala Pro Glu Gln Ser His Val Val Gln Asp Cys Tyr His Gly Asp
20 25 30

Gly Gln Ser Tyr Arg Gly Thr Tyr Ser Thr Thr Val Thr Gly Arg Thr
35 40 45

Cys Gln Ala Trp Ser Ser Met Thr Pro His Gln His Asn Arg Thr Thr
50 55 60

Glu Asn Tyr Pro Asn Ala Gly Leu Ile Met Asn Tyr Cys Arg Asn Pro
65 70 75 80

Asp Ala Val Ala Ala Pro Tyr Cys Tyr Thr Arg Asp Pro Gly Val Arg
85 90 95

Trp Glu Tyr Cys Asn Leu Thr Gln Cys Ser Asp Ala Glu Gly Thr Ala
100 105 110

Val Ala Pro Pro Thr Val Thr Pro Val Pro Ser Leu Glu Ala Pro Ser
115 120 125

Glu Gln Ala Pro Thr Glu Gln Arg Pro Gly Val Gln Glu Cys Tyr His
130 135 140

Gly Asn Gly Gln Ser Tyr Arg Gly Thr Tyr Ser Thr Thr Val Thr Gly
145 150 155 160

Arg Thr Cys Gln Ala Trp Ser Ser Met Thr Pro His Ser His Ser Arg
165 170 175

Thr Pro Glu Tyr Tyr Pro Asn Ala Gly Leu Ile Met Asn Tyr Cys Arg
180 185 190

Asn Pro Asp Ala Val Ala Ala Pro Tyr Cys Tyr Thr Arg Asp Pro Gly
195 200 205

Val Arg Trp Glu Tyr Cys Asn Leu Thr Gln Cys Ser Asp Ala Glu Gly
210 215 220

Thr Ala Val Ala Pro Pro Thr Val Thr Pro Val Pro Ser Leu Glu Ala
225 230 235 240

Pro Ser Glu Gln Ala Pro Thr Glu Gln Arg Pro Gly Val Gln Glu Cys

-continued

```
                245                 250                 255

Tyr His Gly Asn Gly Gln Ser Tyr Arg Gly Thr Tyr Ser Thr Thr Val
            260                 265                 270

Thr Gly Arg Thr Cys Gln Ala Trp Ser Ser Met Thr Pro His Ser His
        275                 280                 285

Ser Arg Thr Pro Glu Tyr Tyr Pro Asn Ala Gly Leu Ile Met Asn Tyr
    290                 295                 300

Cys Arg Asn Pro Asp Ala Val Ala Ala Pro Tyr Cys Tyr Thr Arg Asp
305                 310                 315                 320

Pro Gly Val Arg Trp Glu Tyr Cys Asn Leu Thr Gln Cys Ser Asp Ala
                325                 330                 335

Glu Gly Thr Ala Val Ala Pro Pro Thr Val Thr Pro Val Pro Ser Leu
            340                 345                 350

Glu Ala Pro Ser Glu Gln Ala Pro Thr Glu Gln Arg Pro Gly Val Gln
        355                 360                 365

Glu Cys Tyr His Gly Asn Gly Gln Ser Tyr Arg Gly Thr Tyr Ser Thr
    370                 375                 380

Thr Val Thr Gly Arg Thr Cys Gln Ala Trp Ser Ser Met Thr Pro His
385                 390                 395                 400

Ser His Ser Arg Thr Pro Glu Tyr Tyr Pro Asn Ala Gly Leu Ile Met
                405                 410                 415

Asn Tyr Cys Arg Asn Pro Asp Ala Val Ala Ala Pro Tyr Cys Tyr Thr
            420                 425                 430

Arg Asp Pro Gly Val Arg Trp Glu Tyr Cys Asn Leu Thr Gln Cys Ser
        435                 440                 445

Asp Ala Glu Gly Thr Ala Val Ala Pro Pro Thr Val Thr Pro Val Pro
    450                 455                 460

Ser Leu Glu Ala Pro Ser Glu Gln Ala Pro Thr Glu Gln Arg Pro Gly
465                 470                 475                 480

Val Gln Glu Cys Tyr His Gly Asn Gly Gln Ser Tyr Arg Gly Thr Tyr
                485                 490                 495

Ser Thr Thr Val Thr Gly Arg Thr Cys Gln Ala Trp Ser Ser Met Thr
            500                 505                 510

Pro His Ser His Ser Arg Thr Pro Glu Tyr Tyr Pro Asn Ala Gly Leu
        515                 520                 525

Ile Met Asn Tyr Cys Arg Asn Pro Asp Ala Val Ala Ala Pro Tyr Cys
    530                 535                 540

Tyr Thr Arg Asp Pro Gly Val Arg Trp Glu Tyr Cys Asn Leu Thr Gln
545                 550                 555                 560

Cys Ser Asp Ala Glu Gly Thr Ala Val Ala Pro Pro Thr Val Thr Pro
                565                 570                 575

Val Pro Ser Leu Glu Ala Pro Ser Glu Gln Ala Pro Thr Glu Gln Arg
            580                 585                 590

Pro Gly Val Gln Glu Cys Tyr His Gly Asn Gly Gln Ser Tyr Arg Gly
        595                 600                 605

Thr Tyr Ser Thr Thr Val Thr Gly Arg Thr Cys Gln Ala Trp Ser Ser
    610                 615                 620

Met Thr Pro His Ser His Ser Arg Thr Pro Glu Tyr Tyr Pro Asn Ala
625                 630                 635                 640

Gly Leu Ile Met Asn Tyr Cys Arg Asn Pro Asp Ala Val Ala Ala Pro
                645                 650                 655

Tyr Cys Tyr Thr Arg Asp Pro Gly Val Arg Trp Glu Tyr Cys Asn Leu
            660                 665                 670
```

-continued

```
Thr Gln Cys Ser Asp Ala Glu Gly Thr Ala Val Ala Pro Pro Thr Val
        675                 680                 685

Thr Pro Val Pro Ser Leu Glu Ala Pro Ser Glu Gln Ala Pro Thr Glu
    690                 695                 700

Gln Arg Pro Gly Val Gln Glu Cys Tyr His Gly Asn Gly Gln Ser Tyr
705                 710                 715                 720

Arg Gly Thr Tyr Ser Thr Thr Val Thr Gly Arg Thr Cys Gln Ala Trp
                725                 730                 735

Ser Ser Met Thr Pro His Ser His Ser Arg Thr Pro Glu Tyr Tyr Pro
            740                 745                 750

Asn Ala Gly Leu Ile Met Asn Tyr Cys Arg Asn Pro Asp Ala Val Ala
        755                 760                 765

Ala Pro Tyr Cys Tyr Thr Arg Asp Pro Gly Val Arg Trp Glu Tyr Cys
    770                 775                 780

Asn Leu Thr Gln Cys Ser Asp Ala Glu Gly Thr Ala Val Ala Pro Pro
785                 790                 795                 800

Thr Val Thr Pro Val Pro Ser Leu Glu Ala Pro Ser Glu Gln Ala Pro
                805                 810                 815

Thr Glu Gln Arg Pro Gly Val Gln Glu Cys Tyr His Gly Asn Gly Gln
            820                 825                 830

Ser Tyr Arg Gly Thr Tyr Ser Thr Thr Val Thr Gly Arg Thr Cys Gln
        835                 840                 845

Ala Trp Ser Ser Met Thr Pro His Ser His Ser Arg Thr Pro Glu Tyr
    850                 855                 860

Tyr Pro Asn Ala Gly Leu Ile Met Asn Tyr Cys Arg Asn Pro Asp Pro
865                 870                 875                 880

Val Ala Ala Pro Tyr Cys Tyr Thr Arg Asp Pro Ser Val Arg Trp Glu
                885                 890                 895

Tyr Cys Asn Leu Thr Gln Cys Ser Asp Ala Glu Gly Thr Ala Val Ala
            900                 905                 910

Pro Pro Thr Ile Thr Pro Ile Pro Ser Leu Glu Ala Pro Ser Glu Gln
        915                 920                 925

Ala Pro Thr Glu Gln Arg Pro Gly Val Gln Glu Cys Tyr His Gly Asn
    930                 935                 940

Gly Gln Ser Tyr Gln Gly Thr Tyr Phe Ile Thr Val Thr Gly Arg Thr
945                 950                 955                 960

Cys Gln Ala Trp Ser Ser Met Thr Pro His Ser His Ser Arg Thr Pro
                965                 970                 975

Ala Tyr Tyr Pro Asn Ala Gly Leu Ile Lys Asn Tyr Cys Arg Asn Pro
            980                 985                 990

Asp Pro Val Ala Ala Pro Trp Cys  Tyr Thr Thr Asp Pro  Ser Val Arg
        995                 1000                 1005

Trp Glu  Tyr Cys Asn Leu Thr  Arg Cys Ser Asp Ala  Glu Trp Thr
    1010                 1015                 1020

Ala Phe  Val Pro Pro Asn Val  Ile Leu Ala Pro Ser  Leu Glu Ala
    1025                 1030                 1035

Phe Phe  Glu Gln Ala Leu Thr  Glu Glu Thr Pro Gly  Val Gln Asp
    1040                 1045                 1050

Cys Tyr  Tyr His Tyr Gly Gln  Ser Tyr Arg Gly Thr  Tyr Ser Thr
    1055                 1060                 1065

Thr Val  Thr Gly Arg Thr Cys  Gln Ala Trp Ser Ser  Met Thr Pro
    1070                 1075                 1080
```

```
His Gln His Ser Arg Thr Pro Glu Asn Tyr Pro Asn Ala Gly Leu
    1085                1090                1095

Thr Arg Asn Tyr Cys Arg Asn Pro Asp Ala Glu Ile Arg Pro Trp
    1100                1105                1110

Cys Tyr Thr Met Asp Pro Ser Val Arg Trp Glu Tyr Cys Asn Leu
    1115                1120                1125

Thr Gln Cys Leu Val Thr Glu Ser Ser Val Leu Ala Thr Leu Thr
    1130                1135                1140

Val Val Pro Asp Pro Ser Thr Glu Ala Ser Ser Glu Glu Ala Pro
    1145                1150                1155

Thr Glu Gln Ser Pro Gly Val Gln Asp Cys Tyr His Gly Asp Gly
    1160                1165                1170

Gln Ser Tyr Arg Gly Ser Phe Ser Thr Thr Val Thr Gly Arg Thr
    1175                1180                1185

Cys Gln Ser Trp Ser Ser Met Thr Pro His Trp His Gln Arg Thr
    1190                1195                1200

Thr Glu Tyr Tyr Pro Asn Gly Gly Leu Thr Arg Asn Tyr Cys Arg
    1205                1210                1215

Asn Pro Asp Ala Glu Ile Ser Pro Trp Cys Tyr Thr Met Asp Pro
    1220                1225                1230

Asn Val Arg Trp Glu Tyr Cys Asn Leu Thr Gln Cys Pro Val Thr
    1235                1240                1245

Glu Ser Ser Val Leu Ala Thr Ser Thr Ala Val Ser Glu Gln Ala
    1250                1255                1260

Pro Thr Glu Gln Ser Pro Thr Val Gln Asp Cys Tyr His Gly Asp
    1265                1270                1275

Gly Gln Ser Tyr Arg Gly Ser Phe Ser Thr Thr Val Thr Gly Arg
    1280                1285                1290

Thr Cys Gln Ser Trp Ser Ser Met Thr Pro His Trp His Gln Arg
    1295                1300                1305

Thr Thr Glu Tyr Tyr Pro Asn Gly Gly Leu Thr Arg Asn Tyr Cys
    1310                1315                1320

Arg Asn Pro Asp Ala Glu Ile Arg Pro Trp Cys Tyr Thr Met Asp
    1325                1330                1335

Pro Ser Val Arg Trp Glu Tyr Cys Asn Leu Thr Gln Cys Pro Val
    1340                1345                1350

Met Glu Ser Thr Leu Leu Thr Thr Pro Thr Val Val Pro Val Pro
    1355                1360                1365

Ser Thr Glu Leu Pro Ser Glu Glu Ala Pro Thr Glu Asn Ser Thr
    1370                1375                1380

Gly Val Gln Asp Cys Tyr Arg Gly Asp Gly Gln Ser Tyr Arg Gly
    1385                1390                1395

Thr Leu Ser Thr Thr Ile Thr Gly Arg Thr Cys Gln Ser Trp Ser
    1400                1405                1410

Ser Met Thr Pro His Trp His Arg Arg Ile Pro Leu Tyr Tyr Pro
    1415                1420                1425

Asn Ala Gly Leu Thr Arg Asn Tyr Cys Arg Asn Pro Asp Ala Glu
    1430                1435                1440

Ile Arg Pro Trp Cys Tyr Thr Met Asp Pro Ser Val Arg Trp Glu
    1445                1450                1455

Tyr Cys Asn Leu Thr Arg Cys Pro Val Thr Glu Ser Ser Val Leu
    1460                1465                1470

Thr Thr Pro Thr Val Ala Pro Val Pro Ser Thr Glu Ala Pro Ser
```

-continued

```
    1475                1480                1485

Glu Gln  Ala Pro Pro Glu Lys  Ser Pro Val Val Gln  Asp Cys Tyr
    1490                1495                1500

His Gly  Asp Gly Arg Ser Tyr  Arg Gly Ile Ser Ser  Thr Thr Val
    1505                1510                1515

Thr Gly  Arg Thr Cys Gln Ser  Trp Ser Ser Met Ile  Pro His Trp
    1520                1525                1530

His Gln  Arg Thr Pro Glu Asn  Tyr Pro Asn Ala Gly  Leu Thr Glu
    1535                1540                1545

Asn Tyr  Cys Arg Asn Pro Asp  Ser Gly Lys Gln Pro  Trp Cys Tyr
    1550                1555                1560

Thr Thr  Asp Pro Cys Val Arg  Trp Glu Tyr Cys Asn  Leu Thr Gln
    1565                1570                1575

Cys Ser  Glu Thr Glu Ser Gly  Val Leu Glu Thr Pro  Thr Val Val
    1580                1585                1590

Pro Val  Pro Ser Met Glu Ala  His Ser Glu Ala Ala  Pro Thr Glu
    1595                1600                1605

Gln Thr  Pro Val Val Arg Gln  Cys Tyr His Gly Asn  Gly Gln Ser
    1610                1615                1620

Tyr Arg  Gly Thr Phe Ser Thr  Thr Val Thr Gly Arg  Thr Cys Gln
    1625                1630                1635

Ser Trp  Ser Ser Met Thr Pro  His Arg His Gln Arg  Thr Pro Glu
    1640                1645                1650

Asn Tyr  Pro Asn Asp Gly Leu  Thr Met Asn Tyr Cys  Arg Asn Pro
    1655                1660                1665

Asp Ala  Asp Thr Gly Pro Trp  Cys Phe Thr Thr Asp  Pro Ser Ile
    1670                1675                1680

Arg Trp  Glu Tyr Cys Asn Leu  Thr Arg Cys Ser Asp  Thr Glu Gly
    1685                1690                1695

Thr Val  Val Ala Pro Pro Thr  Val Ile Gln Val Pro  Ser Leu Gly
    1700                1705                1710

Pro Pro  Ser Glu Gln Asp Cys  Met Phe Gly Asn Gly  Lys Gly Tyr
    1715                1720                1725

Arg Gly  Lys Lys Ala Thr Thr  Val Thr Gly Thr Pro  Cys Gln Glu
    1730                1735                1740

Trp Ala  Ala Gln Glu Pro His  Arg His Ser Thr Phe  Ile Pro Gly
    1745                1750                1755

Thr Asn  Lys Trp Ala Gly Leu  Glu Lys Asn Tyr Cys  Arg Asn Pro
    1760                1765                1770

Asp Gly  Asp Ile Asn Gly Pro  Trp Cys Tyr Thr Met  Asn Pro Arg
    1775                1780                1785

Lys Leu  Phe Asp Tyr Cys Asp  Ile Pro Leu Cys Ala  Ser Ser Ser
    1790                1795                1800

Phe Asp  Cys Gly Lys Pro Gln  Val Glu Pro Lys Lys  Cys Pro Gly
    1805                1810                1815

Ser Ile  Val Gly Gly Cys Val  Ala His Pro His Ser  Trp Pro Trp
    1820                1825                1830

Gln Val  Ser Leu Arg Thr Arg  Phe Gly Lys His Phe  Cys Gly Gly
    1835                1840                1845

Thr Leu  Ile Ser Pro Glu Trp  Val Leu Thr Ala Ala  His Cys Leu
    1850                1855                1860

Lys Lys  Ser Ser Arg Pro Ser  Ser Tyr Lys Val Ile  Leu Gly Ala
    1865                1870                1875
```

-continued

```
His Gln  Glu Val Asn Leu Glu  Ser His Val Gln Glu  Ile Glu Val
    1880                 1885                 1890

Ser Arg  Leu Phe Leu Glu Pro  Thr Gln Ala Asp Ile  Ala Leu Leu
    1895                 1900                 1905

Lys Leu  Ser Arg Pro Ala Val  Ile Thr Asp Lys Val  Met Pro Ala
    1910                 1915                 1920

Cys Leu  Pro Ser Pro Asp Tyr  Met Val Thr Ala Arg  Thr Glu Cys
    1925                 1930                 1935

Tyr Ile  Thr Gly Trp Gly Glu  Thr Gln Gly Thr Phe  Gly Thr Gly
    1940                 1945                 1950

Leu Leu  Lys Glu Ala Gln Leu  Leu Val Ile Glu Asn  Glu Val Cys
    1955                 1960                 1965

Asn His  Tyr Lys Tyr Ile Cys  Ala Glu His Leu Ala  Arg Gly Thr
    1970                 1975                 1980

Asp Ser  Cys Gln Gly Asp Ser  Gly Gly Pro Leu Val  Cys Phe Glu
    1985                 1990                 1995

Lys Asp  Lys Tyr Ile Leu Gln  Gly Val Thr Ser Trp  Gly Leu Gly
    2000                 2005                 2010

Cys Ala  Arg Pro Asn Lys Pro  Gly Val Tyr Ala Arg  Val Ser Arg
    2015                 2020                 2025

Phe Val  Thr Trp Ile Glu Gly  Met Met Arg Asn Asn
    2030                 2035                 2040


<210> SEQ ID NO 20
<211> LENGTH: 114
<212> TYPE: PRT
<213> ORGANISM: Artificial Sequence
<220> FEATURE:
<223> OTHER INFORMATION: LPA-KIV9 peptide

<400> SEQUENCE: 20

Cys Arg Asn Pro Asp Ser Gly Lys Gln Pro Trp Cys Tyr Thr Thr Asp
1               5                   10                  15

Pro Cys Val Arg Trp Glu Tyr Cys Asn Leu Thr Gln Cys Ser Glu Thr
            20                  25                  30

Glu Ser Gly Val Leu Glu Thr Pro Thr Val Val Pro Val Pro Ser Met
        35                  40                  45

Glu Ala His Ser Glu Ala Ala Pro Thr Glu Gln Thr Pro Val Val Arg
    50                  55                  60

Gln Cys Tyr His Gly Asn Gly Gln Ser Tyr Arg Gly Thr Phe Ser Thr
65                  70                  75                  80

Thr Val Thr Gly Arg Thr Cys Gln Ser Trp Ser Ser Met Thr Pro His
                85                  90                  95

Arg His Gln Arg Thr Pro Glu Asn Tyr Pro Asn Asp Gly Leu Thr Met
            100                 105                 110

Asn Tyr


<210> SEQ ID NO 21
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 21

Cys Ser Glu Thr Glu Ser Gly Val Leu Glu Thr Pro Thr Val Val
1               5                   10                  15
```

-continued

<210> SEQ ID NO 22
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 22

Ser Glu Thr Glu Ser Gly Val Leu Glu Thr Pro Thr Val Val Pro
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 23

Glu Thr Glu Ser Gly Val Leu Glu Thr Pro Thr Val Val Pro Val
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 24

Thr Glu Ser Gly Val Leu Glu Thr Pro Thr Val Val Pro Val Pro
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 25

Glu Ser Gly Val Leu Glu Thr Pro Thr Val Val Pro Val Pro Ser
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 26

Ser Gly Val Leu Glu Thr Pro Thr Val Val Pro Val Pro Ser Met
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 27

Gly Val Leu Glu Thr Pro Thr Val Val Pro Val Pro Ser Met Glu
1 5 10 15

-continued

<210> SEQ ID NO 28
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 28

Val Leu Glu Thr Pro Thr Val Val Pro Val Pro Ser Met Glu Ala
1 5 10 15

<210> SEQ ID NO 29
<211> LENGTH: 15
<212> TYPE: PRT
<213> ORGANISM: Artificial Sequence
<220> FEATURE:
<223> OTHER INFORMATION: LPA-KIV9 peptide

<400> SEQUENCE: 29

Leu Glu Thr Pro Thr Val Val Pro Val Pro Ser Met Glu Ala His
1 5 10 15

<210> SEQ ID NO 30
<211> LENGTH: 120
<212> TYPE: PRT
<213> ORGANISM: Artificial Sequence
<220> FEATURE:
<223> OTHER INFORMATION: LPA-KIV9 polypeptide

<400> SEQUENCE: 30

Ala Pro Pro Glu Lys Ser Pro Val Val Gln Asp Cys Tyr His Gly Asp
1 5 10 15

Gly Arg Ser Tyr Arg Gly Ile Ser Ser Thr Thr Val Thr Gly Arg Thr
20 25 30

Cys Gln Ser Trp Ser Ser Met Ile Pro His Trp His Gln Arg Thr Pro
35 40 45

Glu Asn Tyr Pro Asn Ala Gly Leu Thr Glu Asn Tyr Cys Arg Asn Pro
50 55 60

Asp Ser Gly Lys Gln Pro Trp Cys Tyr Thr Thr Asp Pro Cys Val Arg
65 70 75 80

Trp Glu Tyr Cys Asn Leu Thr Gln Cys Ser Glu Thr Glu Ser Gly Val
85 90 95

Leu Glu Thr Pro Thr Val Val Pro Val Pro Ser Met Glu Ala His Ser
100 105 110

Glu Ala Ala Pro Thr Glu Gln Thr
115 120

<210> SEQ ID NO 31
<211> LENGTH: 15
<212> TYPE: PRT
<213> ORGANISM: Artificial Sequence
<220> FEATURE:
<223> OTHER INFORMATION: KIV9 peptide

<400> SEQUENCE: 31

Gly Asp Gly Arg Ser Tyr Arg Gly Ile Ser Ser Thr Thr Val Thr
1 5 10 15

<210> SEQ ID NO 32
<211> LENGTH: 10
<212> TYPE: PRT
<213> ORGANISM: Artificial Sequence
<220> FEATURE:

-continued

```
<223> OTHER INFORMATION: KV peptide

<400> SEQUENCE: 32

Met Asn Pro Arg Lys Leu Phe Asp Tyr Cys
1               5                   10


<210> SEQ ID NO 33
<211> LENGTH: 25
<212> TYPE: DNA
<213> ORGANISM: Artificial Sequence
<220> FEATURE:
<223> OTHER INFORMATION: Forward Primer

<400> SEQUENCE: 33

tccactccca ggtccaactg cacct                                          25


<210> SEQ ID NO 34
<211> LENGTH: 32
<212> TYPE: DNA
<213> ORGANISM: Artificial Sequence
<220> FEATURE:
<223> OTHER INFORMATION: Reverse primer

<400> SEQUENCE: 34

gaaccgttac agagaggata tcacagtagt ca                                  32
```

ISOFORM-INDEPENDENT ANTIBODIES TO LIPOPROTEIN(A)

CROSS REFERENCE TO RELATED APPLICATIONS

This application is a U.S. National Phase application filed under 35 U.S.C. § 371 and claims priority to International Application No. PCT/US2021/029307, filed Apr. 27, 2021, which application claims priority to U.S. Provisional Application No. 63/016,017, filed Apr. 27, 2020, the disclosures of which are incorporated herein by reference.

TECHNICAL FIELD

The disclosure provides human and humanized antibodies, single chain variable region (scFv) and binding domains thereof that bind to lipoprotein(a) (Lp(a)). The disclosure relates to methods and compositions to treat patients with antibodies, scFvs and binding domains thereof to treat diseases and disorders associated with Lp(a) and for use in diagnostics.

INCORPORATION BY REFERENCE OF SEQUENCE LISTING

Accompanying this filing is a Sequence Listing entitled "Sequence-Listing_ST25.txt", created on Apr. 27, 2021, and having 34,360 bytes of data, machine formatted on IBM-PC, MS-Windows operating system. The sequence listing is hereby incorporated herein by reference in its entirety for all purposes.

BACKGROUND

Lipoprotein(a) [Lp(a)] is composed of apolipoprotein(a) covalently bound to apolipoprotein B-100. The apolipoprotein(a) protein displays wide size heterogeneity due to a variable number of kringle IV Type 2 (KIV2) repeats among individuals and populations (see, e.g., FIG. 1A). Apolipoprotein(a) consists of 10 unique kringle IV repeats that are present in one copy, except KIV2 which is present in a variable number of identical copies (1 to >40). It also contains one copy of KV and an inactive protease-like domain. Plasma Lp(a) levels are genetically determined by the production rate of apolipoprotein(a) in hepatocytes, with isoforms containing a small number of KIV2 repeats being secreted more efficiently, leading to an inverse association of KIV2 repeat number and plasma Lp(a) levels.

Many assays exist to measure plasma Lp(a), but assay methodologies vary among manufacturers and additionally have not been globally standardized. The variability in the number of repeats in KIV2 has led to significant methodological limitations in accurately measuring plasma Lp(a) levels. All commercially available assays use polyclonal antibodies, which are a mixture of antibodies that may bind multiple times to KIV2 repeats and to other segments of apolipoprotein(a). Furthermore, assay calibrators are derived from pooled plasma of multiple donors and generally cannot represent all known apolipoprotein isoforms of the samples being measured. Relative to the calibrators, polyclonal antibodies tend to bind more frequently to larger apolipoprotein(a) isoforms, which are found in subjects with low plasma Lp(a) and thus tend to overestimate these values. In contrast such antibodies bind less frequently to small isoforms, which are found in Lp(a) in subjects with high plasma Lp(a) and tend to underestimate values. This size dependent bias can be minimized by the use of separate pools of calibrators representing most isoforms, as opposed to serial dilutions on one pool, and also be re-assigning new values to the calibrators with a more accurate method.

It is expected that the testing of Lp(a) values will expand with new guidelines recommending every person have an Lp(a) measured at least once in their lifetime and by the development of new therapies substantially lowering Lp(a). Thus the imperative for accurate methods is stronger than ever.

SUMMARY

The disclosure provides an antibody or antibody fragment that recognizes and binds to lipoprotein(a), wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) selected from the group consisting of: SEQ ID NO:4 or variants thereof, SEQ ID NO:6 or variants thereof, and SEQ ID NO:8 or variants thereof; and (b) the $V_L$ domain comprises an amino acid sequence that includes one, two or three complementarity determining regions (CDRs) selected from the group consisting of: SEQ ID NO:12 or variants thereof, a sequence KVS or variants thereof, and SEQ ID NO:15 or variants thereof, wherein the antibody or antibody fragment comprising CDRs selected from SEQ ID Nos:4, 6, 8, 12, 15 and KVS and combinations of any of the foregoing bind to Lp(a). In one embodiment, the $V_H$ domain comprises an amino acid sequence that includes CDRs comprising SEQ ID NO:4, 6 and 8. In another embodiment, the $V_L$ domain comprises an amino acid sequence that includes CDRs comprising SEQ ID NO:12, 15 and the sequence KVS. In another or further embodiment, the antibody or antibody fragment is selected from the group consisting of an antibody or scFv with heavy and light chain domains comprising the complementarity determining regions of SEQ ID NO:4, 6, 8, 12, 15 and KVS. In yet another or further embodiment, the heavy and light chain domains are linked to an Fc region. In a further embodiment, the Fc region is a human Fc region. In another embodiment, the antibody fragment comprises a single chain variable fragment ("scFv") that recognizes an epitope of KIV9 of lipoprotein (a). In a further embodiment, the epitope comprises or consists of the sequence CSETESGVLETPTVVPVPSMEAH (SEQ ID NO:18; see also SEQ ID NO:19 from amino acid 1579-1601). In one embodiment, the epitope contains SEQ ID NO:18 and includes 1-10 additional amino acids at the N-terminal and/or C-terminal end of SEQ ID NO:18 (additional amino acids can include those 1-10 amino acids N-terminal or C-terminal to SEQ ID NO:19 upstream of amino acid 1579 or downstream of amino acid 1601). In yet another or further embodiment, the scFv is soluble under physiological conditions. In yet another or further embodiment, the scFv comprises a light-chain variable region having a sequence that is at least 95% identical to the sequence as set forth in SEQ ID NO:10. In still a further embodiment, the scFv comprises a heavy chain variable region having a sequence that is at least 95% identical to the sequence as set forth in SEQ ID NO:2.

The disclosure also provides an antibody comprising a variable light chain and variable heavy chain as described in the prior paragraph. In one embodiment, the antibody is humanized. In another embodiment, the antibody is chimeric.

The disclosure also provides a pharmaceutical composition comprising an antibody or antibody fragment of the disclosure and a pharmaceutically acceptable carrier, excipient, and/or stabilizer.

The disclosure also provide an antibody or antibody fragment of the disclosure bound to a solid substrate.

The disclosure also provides an antibody or antibody fragment of the disclosure operably linked to a detectable label.

The disclosure also provides a polynucleotide that encodes an antibody, antibody fragment, variable light chain, variable heavy chain or scFv of the disclosure. In one embodiment, the polynucleotide comprises SEQ ID NO:1 and/or 9 or variants thereof, wherein the polynucleotide encodes a polypeptide that binds to an epitope of KIV9 of Lp(a) containing SEQ ID NO:18.

The disclosure further includes a vector comprising a polynucleotide encoding an antibody or antibody fragment of the disclosure.

The disclosure also provides a host cell transformed with the polynucleotide of the disclosure.

The disclosure also provides a host cell transformed with a vector of the disclosure.

The disclosure also provides a transgenic animal, comprising a polynucleotide encoding an antibody or antibody fragment of the disclosure. In one embodiment, the animal is a mouse. In another or further embodiment, an scFv or antibody of the disclosure is expressed from hepatocytes and/or macrophages of the transgenic animal. In a further embodiment, the transgenic animal is used to model the effects of coronary artery disease or disorders such as aortic stenosis and/or atherosclerosis.

The disclosure also provides a method of treating or preventing coronary artery disease comprising administering an antibody or antibody fragment or scFv of the disclosure to a subject having or at risk of having coronary artery disease, stroke, peripheral arterial disease or calcific aortic stenosis.

The disclosure also provides a chimeric antigen receptor (CAR) comprising a binding domain of the VH and/or VL domains as described above and herein, wherein the CAR binds to Lp(a).

The disclosure also provides an immunological composition comprising an antigenic peptide comprising the sequence LETPTVV (SEQ ID NO:17), or an antigenic peptide comprising or consists of the sequence CSETESGVLETPTVVPVPSMEAH (SEQ ID NO:18; see also SEQ ID NO:19 from amino acid 1579-1601). In one embodiment, the antigenic peptide comprising SEQ ID NO:17 or SEQ ID NO:18 and includes 1-10 additional amino acids at the N-terminal and/or C-terminal end (additional amino acids can include those 1-10 amino acids N-terminal or C-terminal to SEQ ID NO:19 upstream of amino acid 1579 or downstream of amino acid 1601). In one embodiment, a peptide sequence comprising or consisting of SEQ ID NO:17 or 18 is linked to or administered with an adjuvant. The disclosure also provides antibodies (polyclonal or monoclonal) obtained from immunizing a mammal with a peptide of SEQ ID NO:17 or 18.

The disclosure also provides a CAR-T cell comprising the chimeric antigen receptor of the disclosure.

DESCRIPTION OF DRAWINGS

FIG. 4A-D shows LPA-KIV9 epitope mapping using a printed peptide microarray. (A) One hundred overlapping, 15 amino acid peptides differing by only one amino acid residue were synthesized on a membrane (SEQ ID Nos:20-29). (B) LPA-$KIV_9$ binding to peptides: LPA-$KIV_9$ binding to peptide array was tested using biotin-anti-mouse-IgG antibody. (C) LPA-$KIV_9$ binds to peptides 29-37, corresponding to the sequence: CSETESGVLETPTVVPVPSMEAH (SEQ ID NO:18). (D) Epitope modeling. The three-dimensional structure of the LPA-$KIV_9$ epitope was predicted by the Swiss-model server (SEQ ID NO:30). The alignment template SMTL ID was 4dur.2.A, plasminogen, with 61.79% sequence identity. The alignment modeling sequence of apolipoprotein(a) was from Q1386 to C1680. It is predicted that the whole sequence of epitope $^{4061}$CSETESGVLETPTVVPVPSMEAH$^{4090}$ (SEQ ID NO:18) is a surface loop epitope.

DETAILED DESCRIPTION

Figure 1A:
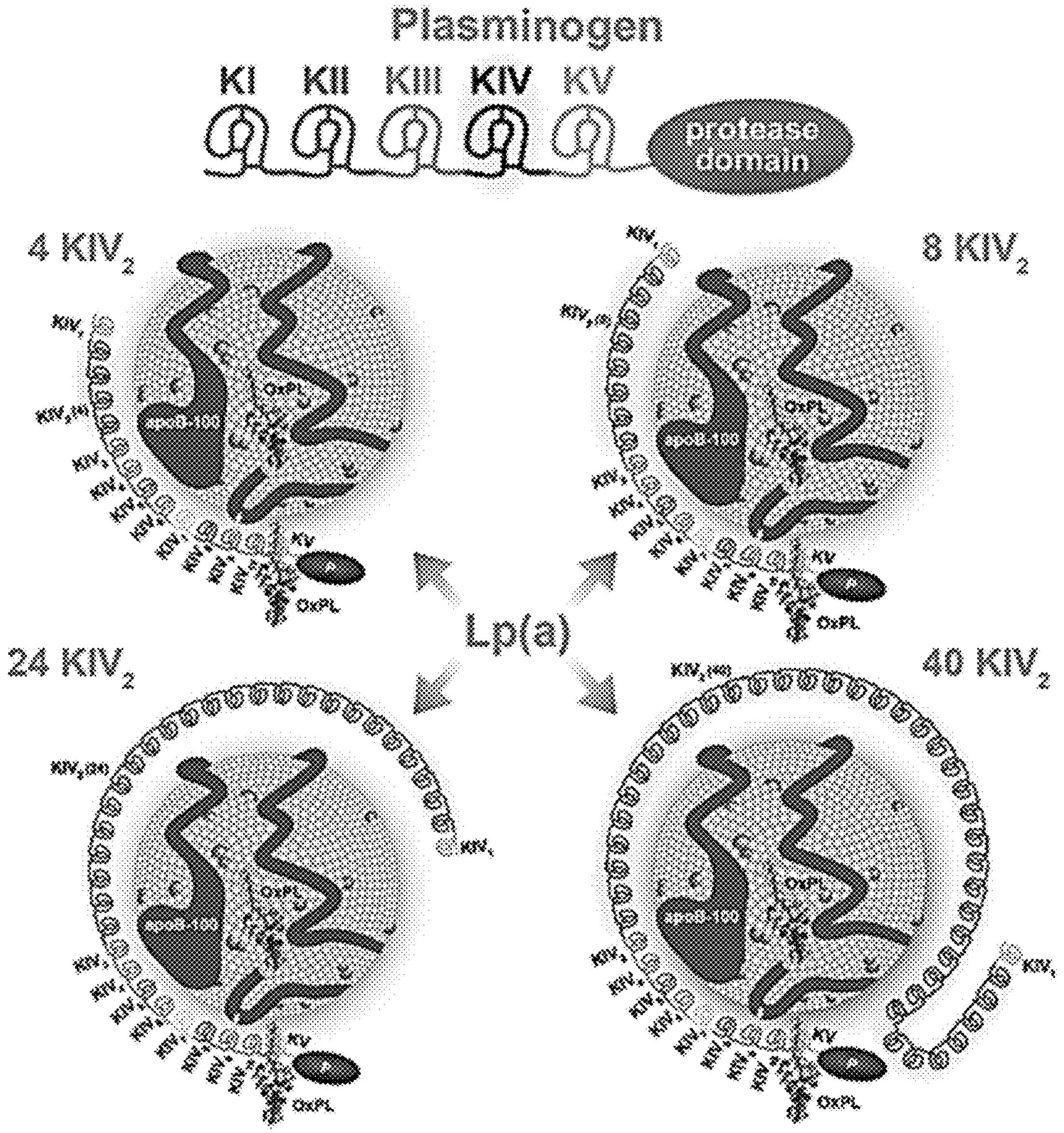
FIG. 1A-E shows (A) a cartoon of apolipoprotein(a) and KIV domains. (B)-(E) show a cartoon of the methodology of Lp(a) and total apo(a) assays. Panels B and C represent Lp(a) and total apo(a) assays, using capture antibodies MB47 and LPA4, respectively, and detecting antibody biotin-LPA4. Panels D and E represent Lp(a) and total apo(a) assays, using capture antibodies MB47 and LPA4, respectively, and detecting antibody biotin-LPA-KIV9.
Figure 1B:
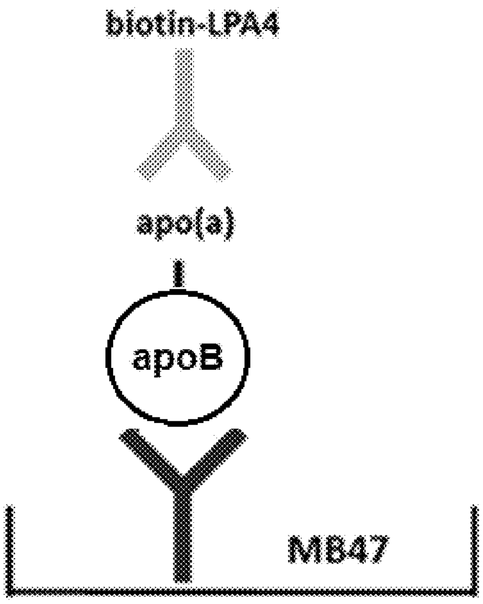
Figure 1C:
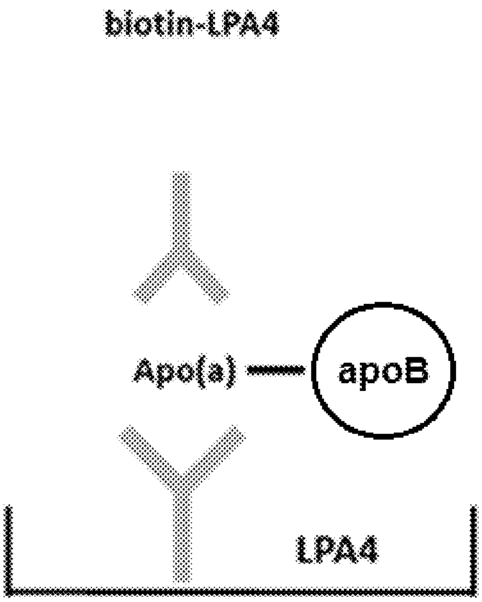
Figure 1D:
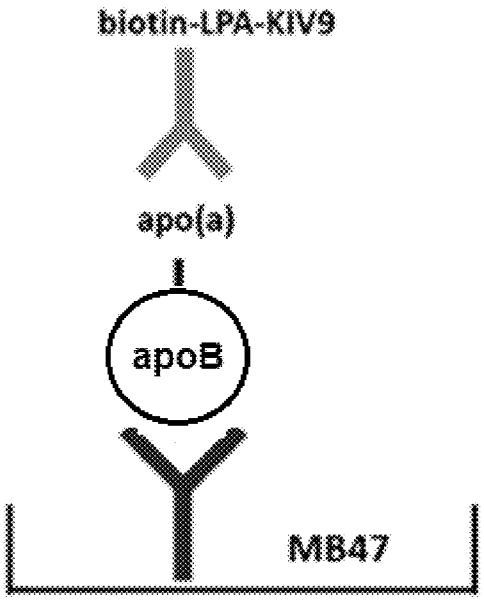
Figure 1E:
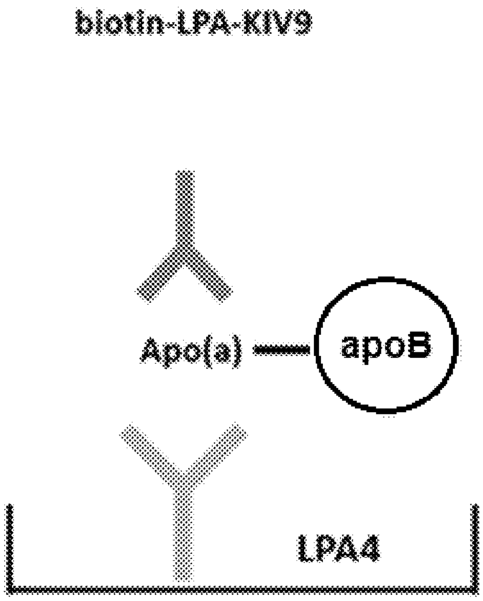

As used herein and in the appended claims, the singular forms "a," "an," and "the" include plural referents unless the context clearly dictates otherwise. Thus, for example, reference to a "single-chain variable fragment" or "scFv"

includes a plurality of single-chain variable fragments and reference to "lipoprotein(a)" includes reference to one or more lipoprotein(a)s and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Lipoprotein(a) (Lp(a)) is common in the human population. There is currently no standardized method or compositions for measuring Lp(a) content in a biological sample. Current antibodies being used to measure Lp(a) bind to kringle repeats (type-2) and thus depending upon how many repeats are present result in obscure measurements. The disclosure provides compositions and methods that measures Lp(a) by binding to non-repeat epitopes. The disclosure provides antibody and antibody fragments that only bind to non-repeats and thus provides a more accurate measurement of Lp(a) content.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods or describe the compositions herein. Moreover, any value or range (e.g., less than 20 or similar terminology) explicitly includes any integer between such values or up to the value. Thus, for example, "one to five mutations" explicitly includes 1, 2, 3, 4, and/or 5 mutations.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and also includes antibody fragments. An antibody can be human, humanized and/or affinity matured.

Depending on the amino acid sequence of the constant domain of the antibody heavy chains, immunoglobulins can be assigned to different classes. There are five major classes of immunoglobulins: IgA, IgD, IgE, IgG, and IgM, and several of these can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are called α, δ, ε, γ, and μ, respectively. The subunit structures and three-dimensional configurations of different classes of immunoglobulins are known.

"Antibody fragments" comprise only a portion of an intact antibody, wherein the portion typically retains at least one, more commonly most, or all, of the functions normally associated with that portion of the antibody when present in an intact antibody. Examples of antibody fragments include Fab, Fab', $F(ab')_2$, and Fv fragments; diabodies; linear antibodies; single-chain antibody molecules (scFv); and multispecific antibodies formed from antibody fragments. In one embodiment, an antibody fragment comprises an antigen binding site of the intact antibody and thus retains the ability to bind its cognate antigen. In another embodiment, an antibody fragment, for example one that comprises the Fc region, retains at least one of the biological functions normally associated with the Fc region when present in an intact antibody, such as FcR binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa (κ) and lambda (λ) light chains refer to the two major antibody light chain isotypes.

An "antigen" is a target to which an antibody can selectively bind. The target antigen may be polypeptide, carbohydrate, nucleic acid, lipid, hapten, small molecule, or other naturally occurring or synthetic compound. In one embodiment of the disclosure an antigen is Lp(a). In another embodiment, the antibody binds to an epitope on the antigen comprising LETPTVV (SEQ ID NO:17) or CSETESGVLETPTVVPVPSMEAH (SEQ ID NO:18).

The term "array," as used herein, generally refers to a predetermined spatial arrangement of binding islands, biomolecules, or spatial arrangements of binding islands or biomolecules. Arrays according to the disclosure that include biomolecules immobilized on a surface may also be referred to as "biomolecule arrays." Arrays according to the disclosure that comprise surfaces activated, adapted, prepared, or modified to facilitate the binding of biomolecules to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass biomolecule arrays, binding arrays, multiple arrays, and any combination thereof; the appropriate meaning will be apparent from context. The biological sample can include fluid or solid samples from any tissue of the body including plasma.

An array of the disclosure comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TEFLON, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from serum. In one embodiment, the biomolecule is an antibody or antibody fragment or derivative of the disclosure.

A planar array of the disclosure will generally contain addressable locations (e.g., "pads", "addresses," or "microlocations") of biomolecules in an array format. The size of the array will depend on the composition and end use of the array. Arrays containing from about 2 different biomolecules to many thousands can be made. In some embodiments, the compositions of the disclosure may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates. In one embodiment, the biomolecule is an antibody or antibody fragment or derivative of the disclosure.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay. In one embodiment, the biomolecule is an antibody or antibody fragment or derivative of the disclosure.

The term "anti-Lp(a) antibody" or "an antibody that binds to Lp(a)" refers to an antibody that is capable of binding Lp(a) with sufficient affinity such that the antibody is useful as a diagnostic and/or therapeutic agent in targeting Lp(a). In some embodiments of the disclosure an anti-Lp(a) antibody binds specifically to $KIV_9$ without binding to $KIV_2$ or plasminogen. In a specific embodiment, the antibody or antibody fragment binds to an epitope containing or comprising LETPTVV (SEQ ID NO:17) or containing or comprising CSETESGVLETPTVVPVPSMEAH (SEQ ID NO:18).

A "blocking" antibody or an "antagonist" antibody is one which inhibits or reduces biological activity of the antigen it binds. Certain blocking antibodies or antagonist antibodies substantially or completely inhibit the biological activity of the antigen. In one embodiment, a blocking antibody binds to its antigen but does not bind an FcR or cause any ADCC. Thus, in one embodiment, the antibody or antibody fragment binds its antigen and prevents or inhibits the antigen's biological activity while the antibody or antibody fragment itself does not induce or has limited effect on the immune system.

"Binding affinity" generally refers to the strength of the sum total of non-covalent interactions between a binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule 'X' for its partner 'Y' can generally be represented by the dissociation constant ($K_d$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the disclosure.

"Binds the same epitope as" means the ability of an antibody, scFv, or other antigen binding domain to bind to a target antigen having the same epitope as the exemplified antibody, scFv, or other antigen binding domain. As an example, the epitopes of the exemplified antibody, scFv, or other binding agent and other antibodies can be determined using standard epitope mapping techniques. Epitope mapping techniques, well known in the art include Epitope Mapping Protocols in Methods in Molecular Biology, Vol. 66 (Glenn E. Morris, Ed., 1996) Humana Press, Totowa, New Jersey. For example, linear epitopes may be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23: 709-715. The epitope bound by the antibody or antibody fragment of the disclosure can be determined by an Epitope Binning assay. Epitope binning is a competitive immunoassay used to characterize and then sort a library of monoclonal antibodies against a target protein. Antibodies against a similar target are tested against all other antibodies in the library in a pairwise fashion to see if antibodies block one another's binding to the epitope of an antigen. After each antibody has a profile created against all of the other antibodies in the library, a competitive blocking profile is created for each antibody relative to the others in the library. Closely related binning profiles indicate that the antibodies have the same or a closely related epitope and are "binned" together. Similarly, conformational epitopes are readily identified by determining spatial conformation of amino acids such as by, e.g., hydrogen/deuterium exchange, x-ray crystallography and two-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al, (1981) Proc. Natl. Acad. Sci USA 78:3824-3828; for determining antigenicity profiles, and the Kyte-Doolittle technique, Kyte et al, (1982) J. Mol. Bioi. 157: 1 05-132; for hydropathy plots. To determine if selected monoclonal antibodies against a target (e.g., Lp(a)) bind to unique epitopes, each antibody can be biotinylated using commercially available reagents. Competition studies using unlabeled monoclonal antibodies and biotinylated monoclonal antibodies can be performed using Lp(a)-coated-ELISA plates. Biotinylated mAb binding can be detected with a strep-avidin-alkaline phosphatase probe.

A "biological sample" encompasses a variety of sample types obtained from an individual and can be used in a diagnostic or monitoring assay. The definition encompasses blood, plasma, serum, sputum, cerebral spinal fluid, urine and other liquid samples of biological origin; solid tissue samples such as a biopsy specimen; or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. In some embodiments, the biological sample is obtained from a site of inflammation, site of a tumor or site of coronary or vascular disease. The biological sample may contain compounds which are not naturally intermixed with the tissue in nature such as preservatives, anticoagulants, buffers, fixatives, nutrients, antibiotics, or the like.

A "conservative substitution" or "conservative sequence modifications" refers to amino acid modifications that do not significantly affect or alter the binding characteristics or function of a protein such as an antibody or antibody fragment. For example, "conservative sequence modifications" refers to amino acid modifications that do not significantly affect or alter the binding characteristics or function of the antibody, antibody fragment, or non-immunoglobulin binding domains. Such conservative modifications include amino acid substitutions, additions and deletions. Modifications can be introduced into an antibody or antibody fragment, the non-immunoglobulin binding domain or other proteins or polypeptides of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within an anti-Lp(a) antibody or fragment of the disclosure can be replaced with other amino acid residues from the same side chain family and the altered antibody or antibody fragment can be tested using the binding and/or functional assays described herein.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993). Triabodies and tetrabodies are also described in Hudson et al., Nat. Med. 9:129-134 (2003).

A "disorder" or "disease" is any condition that would benefit from treatment or diagnosis with a substance/molecule or method of the disclosure. This includes chronic and acute disorders or diseases including those pathological conditions which predispose the mammal to the disorder in question. Non-limiting examples of disorders to be treated herein include cardiovascular disease, stenosis, liver disease (e.g., NASH or NALFD), Kawasaki disease, aging-associated diseases and disorders, senescence or inflammatory diseases attributable to Lp(a).

"Derived from" as that term is used herein, indicates a relationship between a first and a second molecule. It generally refers to structural similarity between the first molecule and a second molecule and does not connotate or include a process or source limitation on a first molecule that is derived from a second molecule. For example, in the case of an antibody fragment that is derived from an antibody molecule, the antibody fragment retains sufficient antibody structure such that is has the required function, namely, the ability to bind to an antigen. It does not connotate or include a limitation to a particular process of producing the antibody fragment.

Antibody "effector functions" refer to those biological activities attributable to the Fc region of an antibody, and vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

As used herein, an "epitope" is defined to be the portion of an antigen capable of eliciting an immune response, or the portion of an antigen that binds to an antibody or antibody fragment. Epitopes can be a protein sequence or subsequence. In one embodiment, an epitope of the disclosure is a peptide that comprises or consists of SEQ ID NO:17 and/or 18.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daeron, Annu. Rev. Immunol. 15:203-234 (1997)). FcRs are reviewed, for example, in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein.

Fc receptor also include the neonatal receptor, FcRn, which is responsible for the transfer of maternal IgGs to the fetus (Guyer et al., J. Immunol. 117:587 (1976) and Kim et al., J. Immunol. 24:249 (1994)) and regulation of homeostasis of immunoglobulins. Methods of measuring binding to FcRn are known (see, e.g., Ghetie and Ward., Immunol. Today 18(12):592-598 (1997); Ghetie et al., Nature Biotechnology, 15(7):637-640 (1997); Hinton et al., J. Biol. Chem. 279(8):6213-6216 (2004); WO 2004/92219 (Hinton et al.).

Binding to human FcRn in vivo and serum half-life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. J. Biol. Chem. 9(2):6591-6604 (2001), each of which is herein incorporated by reference in its entirety.

The term "Fc region" as used herein refers to the C-terminal region of an immunoglobulin heavy chain, including native sequence Fc regions and variant Fc regions.

A "functional Fc region" possesses an "effector function" of a native sequence Fc region. Such effector functions generally require the Fc region to be combined with a binding to domain (e.g., an antibody variable domain) and can be assessed using various assays (e.g., as described in references cited herein).

A "native sequence Fc region" comprises an amino acid sequence that is identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

"Fv" is the minimum antibody fragment which contains a complete antigen-recognition and antigen-binding site. In a two-chain Fv species, this region is composed of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three hypervariable regions (HVRs; sometimes referred to a CDRs) of each variable domain interact to define an antigen-binding site on the surface of the $V_H$-$V_L$ dimer. Collectively, the six HVRs (or CDRs) confer antigen-binding specificity to the antibody. However, even a single variable domain (or half of an Fv comprising only three HVRs specific for an antigen) has the ability to recognize and bind antigen, although at a lower affinity than the entire binding site.

A "Fab fragment" refers to an antibody fragment that contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains have a free thiol group. $F(ab')_2$ antibody fragments originally were produced as pairs of Fab' fragments which have hinge cysteines between them. Other chemical couplings of antibody fragments are also known.

Papain digestion of antibodies produces two identical antigen-binding Fab fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

"Framework" or "FR" residues are those variable domain residues other than the HVR (or CDR) residues as herein defined.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR (CDR) of the recipient are replaced by residues from a HVR (CDR) of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody comprises substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409.

A "human antibody" is an antibody that possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, J. Mol. Biol., 227:381 (1991); Marks et al., J. Mol. Biol., 222:581 (1991), herein incorporated by reference in its entirety. Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol., 5: 368-74 (2001), each of which is herein incorporated by reference in its entirety. Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584). See also, for example, Li et al., Proc. Natl. Acad. Sci. USA, 103:3557-3562 (2006) regarding human antibodies generated via a human B-cell hybridoma technology, each of which is herein incorporated by reference in its entirety.

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

The term "hypervariable region," "HVR," or "HV," (sometimes referred to as "CDR") when used herein refers to the regions of an antibody variable domain which are hypervariable in sequence and/or form structurally defined loops. Generally, antibodies comprise six HVRs (CDRs); three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in Methods in Molecular Biology 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., Nature 363:446-448 (1993); Sheriff et al., Nature Struct. Biol. 3:733-736 (1996).

An "isolated" antibody, antibody fragment and the like refer to an antibody, antibody fragment or derivative, which has been identified and separated and/or recovered from a component of its natural environment. Contaminant components of its natural environment include materials which would interfere with diagnostic or therapeutic uses for the antibody or antibody fragment, and may include enzymes, hormones, lipids, and other proteinaceous or nonproteinaceous solutes. In some embodiments, the antibody or antibody fragment is purified (1) to greater than 95% by weight as determined by the Lowry method, and typically more than 99% by weight, (2) to a degree sufficient to obtain at least 15 residues of N-terminal or internal amino acid sequence by use of a spinning cup sequenator, and/or (3) to homogeneity by SDS-PAGE under reducing or nonreducing conditions using Coomassie blue or silver stain. An isolated antibody or antibody fragment includes the antibody or antibody fragment in situ within recombinant cells since at least one component of the antibody's natural environment is not present. Ordinarily, however, an isolated antibody or antibody fragment is prepared by at least one purification step.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The term "label" when used herein refers to a compound or composition which is conjugated or fused directly or indirectly to a reagent such as a nucleic acid probe or an antibody or antibody fragment and facilitates detection of the reagent to which it is conjugated or fused. The label may itself be detectable (e.g., radioisotope labels, luminescent or fluorescent labels) or, in the case of an enzymatic label, may catalyze chemical alteration of a substrate compound or composition which is detectable.

"Lipoprotein(a)" or "Lp(a)" refer to a low-density lipoprotein variant containing a protein called apolipoprotein(a) (Apo(a)). Genetic and epidemiological studies have identified lipoprotein(a) as a risk factor for atherosclerosis and related diseases, such as coronary heart disease and stroke. Lipoprotein(a) consists of an LDL-like particle and the specific apolipoprotein(a), which is bound covalently to the apoB contained in the outer shell of the particle. Apo(a) proteins vary in size due to a size polymorphism [KIV-2 VNTR], which is caused by a variable number of kringle IV repeats in the LPA gene. This size variation at the gene level is expressed on the protein level as well, resulting in apo(a) proteins with 10 to more than 50 kringle IV repeats (each of the variable kringle IV domains consists of 114 amino acids). These variable apo(a) sizes are known as "apo(a) isoforms". There is a general inverse correlation between the size of the apo(a) isoform and the Lp(a) plasma concentration. Lp(a) concentrations can vary by more than one thousand between individuals, from <0.2 to >200 mg/dL. There is a two- to three-fold higher mean Lp(a) plasma concentration in populations of African descent compared to Asian, Oceanic, or European populations. The general inverse correlation between apo(a) isoform size and Lp(a) plasma concentration is observed in all populations. Cartoon depictions of Lp(a) are provided in FIG. 1A.

Lp(a) contributes to the process of atherogenesis. The structure of apolipoprotein(a) is similar to plasminogen and tPA (tissue plasminogen activator) and it competes with plasminogen for its binding site, leading to reduced fibrinolysis. Also, because Lp(a) stimulates secretion of PAI-1, it leads to thrombogenesis. It also may enhance coagulation by inhibiting the function of tissue factor pathway inhibitor. Moreover, Lp(a) carries atherosclerosis-causing cholesterol and binds atherogenic pro-inflammatory oxidized phospholipids as a preferential carrier of oxidised phospholipids in human plasma, which attracts inflammatory cells to vessel walls and leads to smooth muscle cell proliferation. Lp(a) also is hypothesized to be involved in wound healing and tissue repair by interacting with components of the vascular wall and extracellular matrix. Apo(a), a distinct feature of the Lp(a) particle, binds to immobilized fibronectin thereby providing Lp(a) with the serine-proteinase-type proteolytic activity.

High Lp(a) in blood correlates with coronary heart disease (CHD), cardiovascular disease (CVD), atherosclerosis, thrombosis, and stroke. High Lp(a) correlates with early atherosclerosis independently of other cardiac risk factors, including LDL. In patients with advanced cardiovascular disease, Lp(a) indicates a coagulant risk of plaque thrombosis. Apo(a) contains domains that are very similar to plasminogen (PLG). Lp(a) accumulates in the vessel wall and inhibits the binding of PLG to the cell surface, reducing plasmin generation, which increases clotting. This inhibition of PLG by Lp(a) also promotes the proliferation of smooth muscle cells. These unique features of Lp(a) suggest that Lp(a) causes generation of clots and atherosclerosis. Numerous studies confirming a strong correlation between elevated Lp(a) and heart disease have led to the consensus that Lp(a) is an important independent predictor of cardiovascular disease. Animal studies have shown that Lp(a) may directly contribute to atherosclerotic damage by increasing plaque size, inflammation, instability, and smooth muscle cell growth. Genetic data also support the theory that Lp(a) causes cardiovascular disease. Lp(a) is associated with enhanced atherogenic potential, particularly at levels >30 mg/dl, and is shown to be an independent predictor (odds ratio −1.5-2) of cardiovascular risk, particularly in younger subjects (<60 years old) and those with elevated LDL cholesterol levels.

Lp(a) appears with different isoforms (per kringle repeats) of apolipoprotein; 40% of the variation in Lp(a) levels when measured in mg/dl can be attributed to different isoforms. Lighter Lp(a) are also associated with disease. Thus, a test with simple quantitative results may not provide a complete assessment of risk.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier term "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody for purposes of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier term "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by a variety of techniques, including, for example, the hybridoma method (e.g., Kohler and Milstein, Nature, 256: 495-97 (1975); Hongo et al., Hybridoma, 14 (3): 253-260 (1995), Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage-display technologies (see, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; and U.S. Pat. No. 5,661,016; Marks et al., Bio/Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996); and Lonberg and Huszar, Intern. Rev. Immunol. 13: 65-93 (1995).

A monoclonal antibody herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., Proc. Natl. Acad. Sci. USA 81:6851-6855 (1984)). Chimeric antibodies include antibodies wherein the antigen-binding region of the antibody is derived from an antibody produced by, e.g., immunizing macaque monkeys with the antigen of interest.

"Oligonucleotide," as used herein, refers to short, typically single stranded polynucleotides that are generally, but not necessarily, less than about 200 nucleotides in length. The terms "oligonucleotide" and "polynucleotide" are not mutually exclusive. The description herein for polynucleotides is equally and fully applicable to oligonucleotides.

The term "operably linked" refers to functional linkage or association between a first component and a second component such that each component can be functional. For example, operably linked includes the association between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. In the context of two polypeptides that are operably linked a first polypeptide functions in the manner it would independent of any linkage and the second polypeptide functions as it would absent a linkage between the two.

"Percent identity" in the context of two or more nucleic acids or polypeptide sequences, refers to two or more sequences that share a degree of similarity. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 30 nucleotides (or 10 amino acids) in length, or more preferably over a region that is 100 to 500 or 1000 or more nucleotides (or 20, 50, 200 or more amino acids) in length.

For sequence comparison, generally one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Bioi. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Brent et al., (2003) Current Protocols in Molecular Biology).

Two examples of algorithms that can be used for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Bioi. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Bioi. 48:444-453) algorithm which has been incorporated into the GAP program in the GCG software package (available at [www.]gcg.com), using either a Blossom 62 matrix or a P AM250 matrix, and a gap weight of 16, 14, 12, 10, 8, 6, or 4 and a length weight of 1, 2, 3, 4, 5, or 6.

A "polynucleotide," or "nucleic acid," as used herein, refer to polymers of nucleotides of any length, and include DNA and RNA. The nucleotides can be deoxyribonucleotides, ribonucleotides, modified nucleotides or bases, and/or their analogs that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "protein" or "polypeptide", which terms are used interchangeably herein, comprises one or more chains of chemical building blocks called amino acids that are linked together by chemical bonds called peptide bonds.

"Single-chain Fv" or "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the vL and vH variable regions in either order, e.g., with respect to the N-terminal and C-terminal ends of the polypeptide, the scFv may comprise vL-linker-vH or may comprise vH-linker-vL.

The term "substantially similar" or "substantially the same," as used herein, denotes a sufficiently high degree of similarity between two numeric values (for example, one associated with an antibody of the disclosure and the other associated with a reference/comparator antibody), such that one of skill in the art would consider the difference between the two values to be of little or no biological and/or statistical significance within the context of the biological characteristic measured by the values (e.g., $K_d$ values). The difference between said two values is, for example, less than about 50%, less than about 40%, less than about 30%, less than about 20%, and/or less than about 10% as a function of the reference/comparator value.

The phrase "substantially reduced," "substantially increased," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., $K_d$ values). The difference between said two values is, for example, greater than about 10%, greater than about 20%, greater than about 30%, greater than about 40%, and/or greater than about 50% as a function of the value for the reference/comparator molecule.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions or hypervariable regions (CDRs or HVRs, used interchangeably herein) both in the light-chain and the heavy-chain variable domains. The more highly conserved portions of variable domains are called the framework regions (FR). The variable domains of native heavy and light chains each comprise four FRs, largely adopting a 3-sheet configuration, connected by three HVRs, which form loops connecting, and in some cases forming part of, the 3-sheet structure. The HVRs in each chain are held together in close proximity by the FRs and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

A "variant Fc region" comprises an amino acid sequence which differs from that of a native sequence Fc region by virtue of at least one amino acid modification, typically one or more amino acid substitution(s). Typically, the variant Fc region has at least one amino acid substitution compared to a native sequence Fc region or to the Fc region of a parent polypeptide, e.g. from about one to about ten amino acid substitutions, and typically from about one to about five amino acid substitutions in a native sequence Fc region or in the Fc region of the parent polypeptide. The variant Fc region of a disclosure possesses at least about 80% homology with a native sequence Fc region and/or with an Fc region of a parent polypeptide, at least about 90% homology therewith, and typically at least about 95% homology therewith.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and replicate along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids.

Calcific aortic valve stenosis (CAVS) is the common form of acquired valvular heart disease, present in 3% of the population over 75 years of age. While risk factors are similar for CAVS and atherosclerosis, ~50% or more of patients with CAVS do not have clinically significant coronary artery disease, suggesting related but unique pathophysiology. Although surgical aortic valve replacement (SAVR) remains the gold standard treatment for most patients, at least one third of symptomatic patients with CAVS may not undergo SAVR. To fill this clinical need, transcatheter aortic valve replacement (TAVR) is increasingly being used, but overall survival remains modest due to the advanced age and other co-morbidities. With the aging of the population, the prevalence of CAVS will increase rapidly and portends medical, financial and ethical burdens to healthcare systems worldwide. Hence, identification of causal pathways mediating CAVS can provide novel targets for earlier therapy prior to end-stage disease. One of these pathways involves the lipoprotein (a) [Lp(a)], lipoprotein-associated phospholipase $A_2$ (Lp-$PLA_2$) and lipoprotein(a) (Lp(a)) axis.

The disclosure provides antibodies, antibody fragments and humanized antibodies that bind to Lp(a). Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to tumors, plaques and diseased tissue. For a review of certain antibody fragments, see Hudson et al. (2003) Nat. Med. 9:129-134, herein incorporated by reference in its entirety.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form $F(ab')_2$ fragments (Carter et al., Bio/Technology 10:163-167 (1992), herein incorporated by reference in its entirety). According to another approach, $F(ab')_2$ fragments are isolated directly from recombinant host cell culture. Fab and $F(ab')_2$ fragment with increased in vivo half-life comprising salvage receptor binding epitope residues are described in U.S. Pat. No. 5,869,046, herein incorporated by reference in its entirety. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458, each of which is herein incorporated by reference in its entirety. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

In addition, knowing the sequences of the antibody and antibody fragments, the generation of chimeric antigen receptors (CARs) and derivative (e.g., $1^{st}$ generation, $2^{nd}$ generation, $3^{rd}$ generation CARs) can be developed. Methods of cloning and generating CARs are known in the art.

The disclosure also provides for single chain variable antibody fragments ("scFv"), $V_H$, $V_L$ and complementarity determining regions that selectively bind to lipoprotein(a). The scFvs of the disclosure are soluble and can be readily synthesized. Further, vectors comprising sequences encoding the scFvs disclosed herein enabled the production of a transgenic murine model for further studies of various diseases and research.

The disclosure, although providing specific antibody sequences and antibody sequence fragments having biological activity, is not limited to polypeptides having these specific sequences. In some embodiments, variants having a percent sequence identity with the specific antibody sequences of the disclosure are also provided. In some embodiments, such variants may be selected for use based on one or more desired, enhanced properties. It should be appreciated that certain variants may have an improved function associated with one desired feature (e.g., binding affinity, avoidance of undesired side effects, etc.), but have a less desirable function associated with another desired featured (e.g., stability, specificity, etc.).

In some embodiments, amino acid sequence modification(s) of the antibodies and fragments described herein are contemplated. For example, it may be desirable to improve the binding affinity and/or other biological properties of the antibody or fragment. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody or antibody fragment. Any combination of deletion, insertion, and substitution can be made to arrive at the final construct, provided that the final construct possesses the desired characteristics comprising, at least binding to Lp(a). The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085, herein incorporated by reference in its entirety. Here, a residue or group of target residues are identified (e.g., charged residues such as Arg, Asp, His, Lys, and Glu) and replaced by a neutral or negatively charged amino acid (e.g., Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, Ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody. Polyhistidine tags are also useful for purification.

In certain embodiments, an antibody or antibody fragment of the disclosure is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn of the $CH_2$ domain of the Fc region. See, e.g., Wright et al. (1997) TIBTECH 15:26-32, herein incorporated by reference in its entirety. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

For example, antibody variants are provided having a carbohydrate structure that lacks fucose attached (directly or indirectly) to an Fc region. Such variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004), each of which is herein incorporated by reference in its entirety. Examples of cell lines capable of producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107), each of which is herein incorporated by reference in its entirety.

Antibody variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.), each of which is herein incorporated by reference in its entirety. Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.), each of which is herein incorporated by reference in its entirety.

In certain embodiments, an antibody variant comprises an Fc region with one or more amino acid substitutions which further improve or inhibit/reduce ADCC. Such substitutions may occur in combination with any of the variations described above.

In certain embodiments, the disclosure contemplates an antibody variant that possesses some but not all effector functions, which make it a desirable candidate for many applications in which the half-life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks a particular binding but retains other binding. Non-limiting examples of in vitro assays to assess ADCC activity of a molecule of interest is described in U.S. Pat. No. 5,500,362 (see, e.g. Hellstrom, I., et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)), each of which is herein incorporated by reference in its entirety. Alternatively, non-radioactive assays methods may be employed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998), herein incorporated by reference in its entirety. C1q binding assays may also be carried out to confirm that the antibody is unable to bind C1q and hence lacks CDC activity. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)), each of which is herein incorporated by reference in its entirety. FcRn binding and in vivo clearance/half-life determinations can also be performed using methods known in the art (see, for example, Petkova, S. B. et al., Int'l. Immunol. 18(12):1759-1769 (2006) herein incorporated by reference in its entirety).

Other antibody variants having one or more amino acid substitutions are provided. Sites of interest for substitutional mutagenesis include the hypervariable regions, but FR alterations are also contemplated. Conservative substitutions can also be performed. Amino acid substitutions may be introduced into an antibody of interest and the products screened, e.g., for a desired activity, such as improved antigen binding, decreased immunogenicity, improved ADCC or CDC, etc.

The disclosure provides an antibody or antibody fragment capable of binding to Lp(a), wherein the antibody or antibody fragment comprises a variable heavy chain ($V_H$) domain and/or a variable light chain ($V_L$) domain, and wherein (a) the $V_H$ domain comprises an amino acid sequence that includes one, two or three complementarity determining regions (CDRs) including, but not limited to:
  (i) SEQ ID NO:4 or variants thereof;
  (ii) SEQ ID NO:6 or variants thereof; and/or
  (iii) SEQ ID NO:8 or variants thereof; and
(b) the $V_L$ domain comprises an amino acid sequence that includes one, two or three complementarity determining regions (CDRs) including, but not limited to:
  (i) SEQ ID NO:12 or variants thereof;
  (ii) KVS or variants thereof; and/or
  (iii) SEQ ID NO:15 or variants thereof.

In one embodiment, the antibody or antibody fragment comprises a $V_H$ domain that comprises an amino acid sequence that includes CDRs comprising SEQ ID NO:4, 6, and 8, and/or the $V_L$ domain comprises an amino acid sequence that includes CDRs comprising SEQ ID NO:12, 15, and KVS.

In one embodiment, the disclosure provides an antibody or an scFv selected from the group consisting of an antibody or scFv with heavy and light chain domains comprising the complementarity determining regions of SEQ ID NO:4, 6, 8, 12, 15 and KVS. In one embodiment the scFv is linked to an Fc region.

In one embodiment, the disclosure provides an antibody comprising a light-chain variable region as set forth in SEQ ID NO:10 from amino acid 20 to about 131 (i.e., lacking the signal peptide of SEQ ID NO:10). In another embodiment, the disclosure provides an antibody that comprises a heavy chain variable region comprising a sequence of SEQ ID NO:2 from about 20 to about 133 (i.e., lacking the signal peptide of SEQ ID NO:2).

In one embodiment, the disclosure provides an scFv comprising a linker between the light change variable region and the heavy-chain variable region. The linker can be any number of commonly used peptide linkers. In one embodiment, the linker comprises one or more repeating units of GGGS (SEQ ID NO:16). The repeat of GGGS (SEQ ID NO:16) may be 2, 3, 4 or more times.

In another embodiment, the disclosure comprises a scFv comprising a light chain variable region of SEQ ID NO:10 linked by a peptide linker to a heavy chain variable region of SEQ ID NO:2. In another embodiment, the disclosure provides for an scFv having a light chain that has a polypeptide sequence that has at least 75%, at least 80%, at least 85%, at least 90%, at least 95%, at least 98%, or at least 99% sequence identity to SEQ ID NO:10, and a heavy chain that has a polypeptide sequence that has at least 75%, at least 80%, at least 85%, at least 90%, at least 95%, at least 98%, or at least 99% sequence identity to SEQ ID NO:2 and wherein the scFv selectively binds to a lipoprotein(a).

In yet further embodiments, fusion constructs comprising a first domain comprising SEQ ID NO:2 from amino acid 20 to about 133 or a variant thereof is operably linked to a second domain comprising (i) a detectable label or (ii) a polypeptide of interest. One of skill in the art will recognize that such fusion constructs can be generated using chemical or molecular biology techniques that link a coding sequence comprising a sequence of SEQ ID NO:1 or variants thereof with a coding sequence of, for example, a polypeptide of interest. The coding sequences and domains may be separated by a linker or directly linked.

In yet another embodiment, the disclosure comprises a scFv comprising a light chain variable region of SEQ ID NO:10 linked by a peptide linker to a heavy chain variable region of SEQ ID NO:2.

Nucleic acid molecules encoding the amino acid sequences of the antibodies, antibody fragments and variants of the antibody are prepared by a variety of methods known in the art. For preparing variants such methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

In a particular embodiment, the disclosure provides a polynucleotide encoding a heavy chain of an antibody or antibody fragment of the disclosure comprising (i) a sequence that encodes a polypeptide of SEQ ID NO:2; (ii) a sequence comprising SEQ ID NO:1 or (iii) a sequence that is at least 80% identical and/or hybridizes to a sequence consisting of SEQ ID NO:1.

In a particular embodiment, the disclosure provides a polynucleotide encoding a light chain of an antibody or antibody fragment of the disclosure comprising (i) a sequence that encodes a polypeptide of SEQ ID NO:10; (ii) a sequence comprising SEQ ID NO:9 or (iii) a sequence that is at least 80% identical and/or hybridizes to a sequence consisting of SEQ ID NO:9.

The disclosure further provides for a scFv disclosed herein that further comprises a fragment crystallizable region ("Fc") of an antibody. In a particular embodiment, the Fc region is from a human or humanized antibody and may be modified to modulate the domains biological activity. The Fc region is the tail region of an antibody that interacts with cell surface receptors called Fc receptors and some proteins of the complement system. This property allows antibodies to activate the immune system. In IgG, IgA and IgD antibody isotypes, the Fc region is composed of two identical protein fragments, derived from the second and third constant domains of the antibody's two heavy chains; IgM and IgE Fc regions contain three heavy chain constant domains ($C_H$ domains 2-4) in each polypeptide chain. The Fc regions of IgGs bear a highly conserved N-glycosylation site. Glycosylation of the Fc fragment is essential for Fc receptor-mediated activity. The N-glycans attached to this site are predominantly core-fucosylated diantennary structures of the complex type. In addition, small amounts of these N-glycans also bear bisecting GlcNAc and α-2,6 linked sialic acid residues. The other part of an antibody, called the Fab region, contains variable sections that define the specific target that the antibody can bind. The scFv of the disclosure are comprised of elements from the Fab region. By contrast, the Fc region of all antibodies in a class are the same for each species; they are constant rather than variable. The Fc region is, therefore, sometimes termed the "fragment constant region". Accordingly, the polynucleotide and polypeptide sequences which encode the Fc regions for countless species have already been determined and would be known by one of skill in the art. In a particular embodiment, the disclosure provides for an antibody and antibody fragment polynucleotides encoding SEQ ID NO:2 and/or 10 or a variant thereof that further comprises a polynucleotide sequence which encodes an Fc region.

In a particular embodiment, the disclosure provides for a polynucleotide sequence disclosed herein (e.g., SEQ ID NO:1 and/or 9) that further comprises a polynucleotide sequence which encodes an Fc region.

In a further embodiment, the disclosure provides for a vector which comprises a polynucleotide sequence encoding a an antibody or antibody fragment wherein the polynucleotide comprises SEQ ID NO:1 and/or 9 or sequences having sequence identity of at least 99%, at least 95%, at least 90%, at least 85%, at least 80%, at least 75% or at least 70% identity to SEQ ID NO:1 and/or 9 and which encodes a polypeptide that specifically binds to an lipoprotein(a).

Polynucleotide sequences encoding polypeptide components of the antibody or antibody fragments of the disclosure can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage vectors may be utilized in making a recombinant vector which can be used to transform susceptible host cells such as *E. coli* LE392.

The expression vector of the disclosure may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the (3-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one embodiment, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector (See Table A and B and SEQ ID Nos:1 and 9). The signal sequence selected for the purpose of the disclosure should be one that is recognized and processed (e.g., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another embodiment, the production of the immunoglobulins according to the disclosure can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the disclosure include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. coli* cells are used as hosts for the disclosure. Examples of *E. coli* strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 (U.S. Pat. No. 5,639,635). Other strains and derivatives thereof, such as *E. coli* 294 (ATCC 31,446), *E. coli* B, *E. coli* X 1776 (ATCC 31,537) and *E. coli* RV308 are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally important to select the appropriate bacteria taking into consideration replicability of the replicon in the cells of a bacterium. For example, *E. coli, Serratia*, or *Salmonella* species can be suitably used as the host when well-known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extra-chromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the disclosure are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures.

In one embodiment, the expressed polypeptides are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Large scale or small scale fermentation can be used and can be optimized using skills well known in the art.

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration.

The disclosure further provides for an expression vector which can be replicated in a prokaryotic system or a eukaryotic system, the vector comprising at least one polynucleotide encoding a light and/or heavy chain disclosed herein. In one embodiment, the disclosure provides for an expression vector which comprises a polynucleotide sequence encoding a first sequence having identity of at least 100%, at least 99%, at least 95%, at least 90%, at least 85%, at least 80%, at least 75% or at least 70% identity to SEQ ID NO:1. In another embodiment, a second vector or the same vector comprises a second polynucleotide comprising a sequence having identity of at least 100%, at least 99%, at least 95%, at least 90%, at least 85%, at least 80%, at least 75% or at least 70% identity to SEQ ID NO:9. In a further embodiment, the vector, when expressed, results in an scFv or antibody in a soluble form, and possesses the ability to bind to Lp(a). In yet a further embodiment, the resultant scFv or antibody that is expressed has a sequence identity of at least 100%, at least 99%, at least 95%, at least 90%, at least 85%, at least 80%, at least 75% or at least 70% identity to SEQ ID NO:2 and 10, wherein the polypeptide is expressed in a soluble form and binds Lp(a).

The disclosure further provides for an expression vector which encodes a scFv or antibody disclosed herein that is transferred into a suitable host organism. The suitable host organism is a microorganism, yeast or a mammalian cell system. Typically, the mammalian cell system is monocyte-derived (e.g., macrophages, monocytes, and neutrophils), lymphocyte-derived (e.g., myeloma, hybridoma, and a normal immortalized B cell), parenchymal (e.g., hepatocytes) and non-parenchymal cells (e.g., stellate cells).

The scFv disclosed herein which further comprises an Fc region, can be used for many possible therapeutic uses. For example, they can be used as an anti-atherosclerotic agent.

In one embodiment, of the disclosure a method for determining a subject's Lp(a) amounts and/or predisposition to coronary artery disease is provided. The method includes determining a subject's plasma Lp(a) and correlating the Lp(a) level control or normal levels, wherein increased levels of Lp(a) are indicative of a predisposition to coronary artery disease. The amount of Lp(a) can be detected using an antibody, antibody fragment or binding domain comprising the CDRs for the light and heavy chains as described herein that specifically binds to an Lp(a). The disclosure can further use a second antibody that binds to OxPL such as E06.

The method can be carried out on a biological sample obtained from a subject. The biological sample can be, for example, blood, serum, or plasma.

In some embodiments, the antibody, antibody fragment or binding domain are immobilized on a substrate to form an array.

An exemplary biochemical test for identifying Lp(a), employs a standardized test format, such as the Enzyme Linked Immunosorbent Assay or ELISA test, although the information provided herein may apply to the development of other biochemical or diagnostic tests and is not limited to the development of an ELISA test. Various commercially available ELISA kits are available.

In one embodiment, an immunoassay can be performed either by first capturing the Lp(a) on a microtiter well by use of an antibody of the disclosure, and then detection of the Lp(a) by a labeled antibody.

The disclosure also provides that a scFv or an antibody of the disclosure can be used as an anti-atherosclerotic agent to treat cardiovascular disease and CAVS. A scFv or antibody of the disclosure can be used to treat high risk patients with coronary artery disease ("CAD"), by inhibiting clot formation induced by the prothrombotic activity of Lp(a).

The scFvs and antibodies disclosed herein can bind to Lp(a)s and block the formation of plaques, clot and/or atherogenesis. It is anticipated that the in vivo use of an scFv, antibody or antibody fragment of the disclosure can be used to block Lp(a) biological effects in many different situations.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, a scFv, antibody or antibody fragment of the disclosure are used to delay development of a disease or disorder.

An "individual," "subject," or "patient" is a vertebrate. In certain embodiments, the vertebrate is a mammal. Mammals include, but are not limited to, farm animals (such as cows), sport animals, pets/companion animals (such as cats, dogs, and horses), primates, mice and rats. In certain embodiments, a mammal is a human.

An "effective amount" refers to an amount effective, at dosages and for periods of time necessary, to achieve the desired therapeutic or prophylactic result.

A "therapeutically effective amount" of a substance/molecule of the disclosure, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

Therapeutic formulations comprising an antibody or fragment thereof of the disclosure are prepared for storage by mixing the antibody or fragment having the desired degree of purity with optional physiologically acceptable carriers, excipients or stabilizers (Remington: The Science and Practice of Pharmacy 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Anti-Lp(a) antibodies of the disclosure can be produced transgenically through the generation of a mammal or plant that is transgenic for the immunoglobulin heavy and light chain sequences of interest and production of the antibody in a recoverable form therefrom. In connection with the transgenic production in mammals, anti-Lp(a) antibodies can be produced in, and recovered from, the milk of goats, cows, or other mammals. See, e.g., U.S. Pat. Nos. 5,827,690, 5,756,687, 5,750,172, and 5,741,957, incorporated herein by reference.

In some embodiments, non-human transgenic animals or plants are produced by introducing one or more nucleic acid molecules encoding an anti-Lp(a) antibody or fragment thereof (e.g., SEQ ID NO:1 and/or 9) of the disclosure into the animal or plant by standard transgenic techniques. See Hogan and U.S. Pat. No. 6,417,429. The transgenic cells used for making the transgenic animal can be embryonic stem cells or somatic cells or a fertilized egg. The transgenic non-human organisms can be chimeric, nonchimeric heterozygotes, and nonchimeric homozygotes. See, e.g., Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999), all incorporated herein by reference. In some embodiments, the transgenic non-human animals have a targeted disruption and replacement by a targeting construct that encodes a heavy chain and/or a light chain of interest. In another embodiment, the transgenic animals comprise and express nucleic acid molecules encoding heavy and light chains that specifically bind to epitopes on Lp(a). In some embodiments, the transgenic animals comprise nucleic acid molecules encoding a modified antibody such as a single-chain antibody, a chimeric antibody or a humanized antibody. The anti-Lp(a) antibodies may be made in any transgenic animal. In another embodiment, the non-human animals are mice, rats, sheep, pigs, goats, cattle or horses. The non-human transgenic animal expresses said encoded polypeptides in blood, milk, urine, saliva, tears, mucus and other bodily fluids.

As described above and in additional detail in the Examples, the disclosure provides a novel murine monoclonal antibody, LPA-KIV9, that detects a unique 23-amino acid epitope on KIV9 of apolipoprotein(a) present only in one copy. LPA-KIV9 successfully quantitated a wide range of plasma Lp(a) levels in a chemiluminescent ELISA format and demonstrated staining of human carotid endarterectomy specimens. This antibody can be used in research settings to immunologically detect apolipoprotein(a) and in clinical settings to measure plasma Lp(a) levels. Since it is a monoclonal antibody binding only one unique epitope of apolipoprotein(a), it may overcome many of the current limitations in measuring Lp(a) levels.

Increasing evidence suggests that Lp(a) is an independent, genetic and likely causal risk factor for cardiovascular disease (CVD). Elevated Lp(a) confers higher risk for myocardial infarction, stroke, peripheral arterial disease and calcific aortic valve stenosis. The association of Lp(a) with risk of CVD is approximately linear, reaching 2-4 fold higher risk at the highest Lp(a) levels. Lp(a) levels may vary more than 1000-fold between individuals, from <0.1 to >300 mg/dL (>750 nmol/L).

Elevated Lp(a) is highly prevalent, with an estimated 20% of the population having levels >50 mg/dL (>125 nmol/L), the threshold above which risk accrues in statin-treated patients. Furthermore, it is a target of therapy to reduce risk of cardiovascular disease, with recent studies showing that antisense oligonucleotides may lower Lp(a) by over 80%, paving the way for a phase 3 clinical trial that is now underway (Lp(a) HORIZON, Assessing the Impact of Lipoprotein(a) Lowering With TQJ230 on Major Cardiovascular Events in Patients With CVD, [https://]clinicaltrials.gov/ct2/show/NCT04023552). Furthermore, multiple national and international societies have suggested that Lp(a) be measured in individuals at moderate to high risk for CVD to enhance risk prediction or for considerations as a risk enhancer. The EAS/ESC has also recommended Lp(a) be measured at least once in everyone's lifetime to assess cardiovascular risk, creating a strong imperative to develop more accurate methods to measure Lp(a) in the clinic.

In 2018, an NHLBI Working Group recommended the development of a globally-standardized measurement of Lp(a) applicable to commercial laboratories. The current methods of measuring Lp(a) are either to 1): assign target values to the assay calibrators in terms of total Lp(a) mass [apo(a), apoB, lipid and carbohydrate components] and represent values in mg/dL. These methods however are limited in having no traceability of the various calibrators to any established reference material; or 2): assign target values to assay calibrators traceable to the World Health Organization/International Federation of Clinical Chemistry and Laboratory Medicine secondary reference material PRM-2B and representing values in nmol/L (i.e. molar concentration of Lp(a) particles). The NHLBI group also recommended that reporting total Lp(a) mass in mg/dL be discontinued and instead that values should be reported in nmol/L traceable to a common reference system. Furthermore, harmonization of results obtained by the different methods should be performed after an accuracy-based common calibration is performed.

The lack of widely-available monoclonal antibodies to Lp(a) that do not bind to either KIV2 repeats or cross-react with plasminogen, which has substantial homology to apolipoprotein(a), has hindered both the accurate measurement of Lp(a) levels as well as the global standardization of Lp(a) assays. The difficulty in generating monoclonal antibodies to Lp(a) suggests that only a limited number of antigenic sites are available to generate such antibodies. One such monoclonal antibody described is a40 which binds to an unknown site on KIV9 and has been used in an ELISA format to measure Lp(a). An ELISA format using a capture antibody detecting KIV2 and a second detection antibody that only binds to one unique site on apolipoprotein(a), along with calibrators traced to the WHO/IFCC, is thought to be the optimal method to reducing size dependent bias. The disclosure provides methods and compositions to carry out and such an ELISA and methods.

Since commercially available assays generally use polyclonal antibodies, these antibodies are isoform-dependent by virtue of binding multiple times to the identical KIV2 repeat segment. In some assays, bias to apolipoprotein(a) size can be somewhat minimized by the use of independent calibrators each containing a suitable distribution of apo(a) isoforms and that have been accurately assigned values by a separate isoform independent assay. Despite this, most assays remain sensitive to apolipoprotein(a) size due to a lack of a consistent relationship between Lp(a) levels and apo(a) isoform size. For this reason, high or low Lp(a) levels may be observed in samples encompassing a relatively large range of apolipoprotein(a) size. Reflecting the size heterogeneity bias, a recent study evaluating Lp(a) levels by 6 commercially available methods concluded that current commercial immunological assays are differently-calibrated and their biases differed significantly across the clinically-relevant concentration range in a non-linear manner not entirely dependent on apolipoprotein(a) phenotypes. Based on these findings, it was suggested that global harmonization of methods is required with further improvement in methodological techniques.

The disclosure demonstrates that LPA-KIV9 can be used successfully to measure Lp(a) levels and compares favorably to previously validated in-house research assays. The current data also shows a significant correlation between "true Lp(a)" versus "total apo(a)" assays. Since in most setting there is a minimal amount of circulating free apolipoprotein(a), this type of distinction is not usually needed. However, in the current PCSK9 inhibitor era it is possible that these assays may provide a method to ascertain the nature of circulating Lp(a)/apolipoprotein(a) particles as suggested.

The following examples are intended to illustrate but not limit the disclosure. While they are typical of those that might be used, other procedures known to those skilled in the art may alternatively be used.

EXAMPLES

Materials: TRIzol® Reagent (Ambion, Cat. No.: 15596-026); PrimeScript™ 1st Strand cDNA Synthesis Kit (Takara, Cat. No.: 6110A). Total RNA was isolated from the hybridoma cells following the technical manual of TRIzol® Reagent. Total RNA was then reverse-transcribed into cDNA using either isotype-specific anti-sense primers or universal primers following the technical manual of PrimeScript™ 1st Strand cDNA Synthesis Kit. Antibody fragments of heavy chain and light chain were amplified according to the standard operating procedure (SOP) of rapid amplification of cDNA ends (RACE) of GenScript. Amplified antibody fragments were cloned into a standard cloning vector separately. Colony PCR was performed to screen for clones with inserts of correct sizes. The consensus sequence was provided.

Generation of immunogens and antigens. To generate immunogens, two approaches were used: First, several truncated apolipoprotein(a) proteins were generated for use as immunogens. One construct spanned the entire $KIV_{10}$-KV sequence and its generation and purification is described below. A second large apolipoprotein(a) construct, designated 8K-IV, contained one copy of $KIV_1$, one copy of $KIV_2$, a fusion of $KIV_3$ and $KIV_5$, and individual kringles $KIV_6$ to $KIV_{10}$, KV, and the protease-like domain, as previously described (Schneider et al., J. Lipid Res. 46:769-778, 2005). As a second strategy, several unique short peptides derived from apolipoprotein(a), but not present on plasminogen were generated, which were conjugated to keyhole limpet hemocyanin (KLH) for immunization. These included peptide GDGRSYRGISSTTVT (SEQ ID NO:31) present in one copy on $KIV_9$ and peptide MNPRKLFDYC (SEQ ID NO:32) present in one copy on KV.

Generation of KIV10-KV construct. To generate the $KIV_{10}$-KV construct, an expression plasmid encoding a sequence spanning the entire KIV10 and KV domains was generated by amplification of the pRK5haKIV10-P plasmid from the apo(a) signal sequence to the end of KV using the following primers set: sense 5'-TCCACTCCCAGGTCCAACTGCACCT-3' (SEQ ID NO:33) and antisense 5'-GAACCGTTACAGAGAGGATATCACAGTAGTCA-3' (SEQ ID NO:34) The sense oligonucleotide binds upstream of the EcoRI site that precedes the sequence encoding the signal sequence; the lower case letters in the antisense oligonucleotide indicate substitutions introduced to generate an AgeI restriction digest site which allows in-frame fusion of the KIV10-KV coding sequence with a carboxyl-terminal 6×His tag in the destination plasmid. PCR reactions were carried out in a BioRad CFX96 thermocycler using Q5 High-Fidelity DNA Polymerase (New England Biolabs) under the following conditions: denaturation at 98° C. (10 sec), annealing at 62° C. (30 sec), and elongation at 72° C. (20 sec), for a total of 40 cycles. The PCR product was digested with EcoRI-HF and AgeI-HF (New England Biolabs) and ligated into the pcDNA4/myc-His expression plasmid also digested with these enzymes (thereby deleting the myc-tag from the final construct) The plasmid was transfected into HEK293 cells using MegaTran1.0 at 10 μg DNA/100 mm plate and subjected to selection with 150 μg/mL Zeocin at 48 hours post-transfection, until a viable population was observed. The KIV10 KV protein was purified from the conditioned medium (CM) of stably-expressing cell lines. The CM was adjusted to 20 mM Tris pH 8.0, 0.5 M NaCl 0.2 mM β-mercaptoethanol, 5 mM imidazole, and 2% glycerol, and applied to a Ni2+-Sepharose excel (GE Healthcare) column; the column was washed and eluted with this buffer containing 12 mM and 300 mM imidazole, respectively. Eluted samples were concentrated with PEG-20,000 (Sigma) and dialyzed against HEPES-buffered saline (HBS; 20 mM HEPES pH 7.4, 150 mM NaCl). Protein concentrations were determined using bicinchoninic acid assay (BCA assay; Pierce) with BSA as a standard. Purity of KIV10 KV was assessed by SDS-PAGE followed by silver staining.

Screening antigens included Lp(a) purified from a single donor as previously described (Van der Valk et al., Circulation, 134:611-624, 2016), human plasminogen (R&D, Minneapolis, MN), and a variety of recombinant apolipoprotein(a) constructs, including 2 $KIV_2$ constructs containing either 3 or 5 copies, constructs spanning consecutively from $KIV_6$ to the protease domain, respectively ($KIV_{6-P}$, $KIV_{7-P}$, $KIV_{8-P}$, $KIV_{9-P}$, $KIV_{10-P}$, respectively), a 17K human construct with $8KIV_2$ repeats, a 17K construct without the protease domain (17KΔP) and a 17K construct without KV (17KΔV).

The disulfide bond between apoB-100 and apolipoprotein (a) is composed of cysteine 4236 of apoB-100 and cysteine 4057 on apolipoprotein(a). Murine monoclonal antibody MB47 specific for human apo B-100, whose epitope on apoB for MB47 is between residues 3350 and 3506, was used in an ELISA format to measured Lp(a). Similarly, murine monoclonal antibody LPA4 that binds to the 14-amino acid epitope TRNYCRNPDAEIRP (see, SEQ ID NO:19 from amino acid 1433 to 1446) present on $KIV_5$, $KIV_7$ and $KIV_8$ of apolipoprotein(a) was used in chemiluminescent ELISAs. The partial sequence of NYCRNPDA (SEQ ID NO:19 from amino acid 75 to 82) detected by LPA4 is also present on $KIV_2$ and is immunologically dominant as LPA4 also binds to $KIV_2$.

Immunization of mice and generation and purification of monoclonal antibodies. All animal experiments were conducted according to protocols approved by the Institutional Animal Care and Use Committee. BALB/C mice were immunized intraperitoneally (IP) with KLH-conjugated peptides GDGRSYRGISSTTVT (SEQ ID NO:31) and MNPRKLFDYC (SEQ ID NO:32), as well as apolipoprotein(a) construct $KIV_{10}$-KV, but these immunogens produced no specific antibodies or the resulting antibodies bound to $KIV_2$ and/or plasminogen, therefore no further work was performed with them and the results are not presented.

A BALB/C mouse was then immunized IP with a primary boost of 125 μg purified 8K-IV apolipoprotein(a), followed at two-week intervals with 3 IP boosts with 75 mg mixed with incomplete Freund's adjuvant (Sigma-Aldrich, St. Louis, MO). A final antigen boost of 25 μg 8K-IV in phosphate-buffered saline (PBS) was administered intravenously two weeks after the 3rd boost. Three days later, the mouse was sacrificed, splenocytes were collected and fused with myeloma cells (p3X63Ag8.653) using a ClonaCell™-HY Hybridoma kit (StemCell Technologies, Cambridge, MA), and the fused cells were resuspended in semi-solid HAT hybridoma selection medium. After 10-14 days, visible colonies were transferred to ClonaCell®-HY Growth Medium (DMEM, pre-selected serum, HT, gentamycin, and supplements).

To select colonies expressing antibodies specific to Lp(a) without binding to plasminogen or $KIV_2$, conditioned media from the hybridoma cells were screened by ELISA as described below. To ensure monoclonality, selected clones that bound Lp(a) but not $KIV_2$ or plasminogen were subcloned twice by limiting dilution in semi-solid gel, without HAT, and re-tested by ELISA. The resulting heavy and light chains of two colonies were sequenced by Genscript (Piscataway, NJ), which were identical in sequence. The cells were expanded by BioXCell (West Lebanon, NH) in tissue culture in a stirred tank fermentation with Hybridoma-SFM medium supplemented with 1% Fetal Clone 3 (Life Technologies, Carlsbad, CA) and antibody purified with chromatography over Protein A/G resin. Determination of antibody isotype was carried out using the IsoStrip Mouse Monoclonal Antibody Isotyping kit (Roche Diagnostics, Vilvoorde, Belgium). This monoclonal antibody was designated as "LPA-$KIV_9$".

ELISA with direct antigen plating to assess binding of hybridoma generated antibodies. Titrations of antibodies present in immunized mouse plasma, screening of hybridoma conditioned media and testing the purified monoclonal antibody were performed by chemiluminescent ELISA. In brief, 96-well microtiter plates (Brand, Germany) were coated directly with Lp(a), apolipoprotein(a) $KIV_2$, or plasminogen) at 5 μg/ml in PBS overnight at 4° C. Non-specific sites were blocked with 1% bovine serum albumin (Gemini Bio-products, CA, USA) in tris-buffered saline) (TBS (1% BSA-TBS) and incubated for 30 min at room temperature. Subsequently, serial dilutions of mouse plasma (1:50-1:400) in 1% BSA-TBS or hybridoma conditioned media (undiluted) were added and incubated for 60 min at room temperature. Bound IgG antibodies were detected using an anti-mouse IgG-alkaline phosphatase (ALP) conjugate (Sigma-Aldrich, St. Louis, MO), Lumi-Phos 530 substrate (Lumigen, Southfield, MI) and a luminescence plate reader (BioTek, Vermont). Antibody binding was expressed as relative light units detected over 100 milliseconds (RLU/100 ms).

Immunoblot analyses. An array of apo(a) constructs was subjected to gel electrophoresis and immunoblot analysis with LPA-KIV9. Briefly, samples (250 ng/well) were loaded in reducing loading buffer and run on a 4-12% Bis-Tris gel (Life Technologies). Gels were transferred to a PVDF membrane (Life Technologies), and the membranes were blocked with 5% nonfat dry milk in Tris-buffered saline and Tween (TBST) for 1 hour before incubation with primary antibodies (1 μg/ml in 1% BSA-TBST) overnight at 4° C., followed by incubation with secondary antibodies conjugated with horse-radish peroxidase (Cell Signaling Technology, Beverly, MA) for 1 hour at room temperature and by detection with KPL-TMB membrane peroxidase substrate (SeraCare, Milford, MA, USA). A dot-blot was also performed with antigens in PBS (25 ng/dot) loaded directly on the membrane. Blocking and immunoblotting were done as described above and detected by a Super Signal West Dura substrate (Thermo Fisher Scientific, Waltham, MA) and an OptiChem HR imaging system (UVP, Upland, CA).

Peptide library array to determine peptide antigen of LPA-$KIV_9$. A peptide library array spanning $KIV_9$, consisting of 100 overlapping, 15 amino acid peptides differing by only one amino acid residue was synthesized on cellulose membranes (JPT, Germany). LPA-$KIV_9$ binding was detected using anti-mouse IgG antibody conjugated with horse-radish peroxidase and SuperSignal West Dura HRP chemiluminescent substrate (Thermo Scientific, USA). Swiss-model structure online analysis software was used to simulate the epitope location on a three-dimensional structural model of $KIV_8$, $KIV_9$, $KIV_{10}$. The alignment template SMTL ID was 4dur.2.A, plasminogen, with 61.79% sequence identity. The alignment modeling sequence of apolipoprotein(a) was from A3866 to V4190.

Sandwich-type Lp(a) chemiluminescent ELISAs to measure plasma Lp(a) in human samples. Previously validated Lp(a) ELISAs measuring "true Lp(a)" with an anti-apoB-100 capture antibody and "total apo(a)", using an anti-apolipoprotein(a) capture antibody (the latter is what most commercial assays measure but call Lp(a)), were utilized for comparisons (Tsimikas et al., J. Clin. Lipidol. 12: 1313-1323, 2018). These assays were previously documented to have adequate linearity in most of the range of Lp(a) levels with plasma dilution at 1:400, analytical range of 1-250 nmol/L, lower limit of detection ~1 nmol/L, to have high levels of reproducibility and intra- and inter-assay variability, and coefficients of variability of 5-10% (Id).

ELISAs of similar format and conditions were then developed with biotin-LPA-$KIV_9$ (EZ-Link™ NHS-PEG4-Biotinylation Kit, Thermo Scientific, Rockford, IL). A schematic of the assay methodologies is shown in FIG. 1. In brief, microtiter well plates were coated with either MB47 to bind human apoB-100 or LPA4 to bind apolipoprotein(a) at 5 μg/ml in PBS overnight at 4° C., followed by blocking with 1% BSA-TBS for 30 minutes at room temperature. Lp(a) or total apo(a) were detected with either biotin-LPA4 or biotin-LPA-$KIV_9$, respectively. It was reconfirmed that a 1:400 dilution of plasma samples is within the linear range and that spiking and recovery experiments with purified Lp(a) resulted in recovery of 95-105% of Lp(a) added.

Pre-existing human plasma samples (n=100), stored at −70° C. for <1 year, with previously measured Lp(a) that had a broad range, were used to measure Lp(a) levels with the 4 assays. Apolipoprotein(a) isoform sizes were not available for these subjects. The protocol was approved by the Human Subjects Protection program and all study subjects gave written informed consent. In brief, the plasma samples were diluted 1:400 in 1% BSA-TBS, added to the microtiter wells containing the capture antibodies and incubated at room temperature for 60 min. After washing the wells, biotin-LPA4 (2 μg/ml) or biotin-LPA-$KIV_9$ (5 μg/ml) were added, the wells washed again and streptavidin-alkaline phosphatase (Thermo Fisher, USA) added. After a final wash step, Lumi-Phos 530 (Southfield, Michigan) was added. A standard curve using serial dilutions of a single calibrator with values assigned in nmol/L traced to the World Health Organization/International Federation of Clinical Chemistry and Laboratory Medicine standard was used.

Immunohistochemistry. Carotid endarterectomy specimens were obtained from carotid endarterectomy surgery. Paraffin embedded carotid endarterectomy specimens were cut into 7 μm thick sections and mounted on charged slides. The sections were deparaffinized with Histoclear and rehydrated through graded ethanol. For antigen retrieval, sections were incubated with Sodium Citrate buffer (pH 6.0) in water bath at 95-100° C. for 20 min, then blocked with 5% normal goat serum/1% BSA/TBS for 30 min at room temperature. LPA4 or LPA-$KIV_9$ monoclonal antibodies (diluted with blocking buffer to 5 μg/ml and 20 μg/ml, respectively) were used to stain sections in a humidified chamber at 4° C. overnight. Sections were then incubated with an anti-mouse IgG-ALP (Sigma A3438) diluted with blocking buffer at 1:50 for 30 min at room temperature, and then visualized with Vector Red substrate (Vector SK-5100). Sections were counterstained with hematoxylin for 30 seconds and mounted with Simpo-Mount (IHCWorld E03-18).

Immunostaining of consecutive sections in the absence of primary Abs was used as a negative control. Images were captured with Hamamatsu Nanozoomer 2.0HT slide scanner with a 20× lens.

Statistics. Descriptive statistical analysis and correlation analysis were performed with Spearman's rho test using SPSS version 26.

Figure 2A:
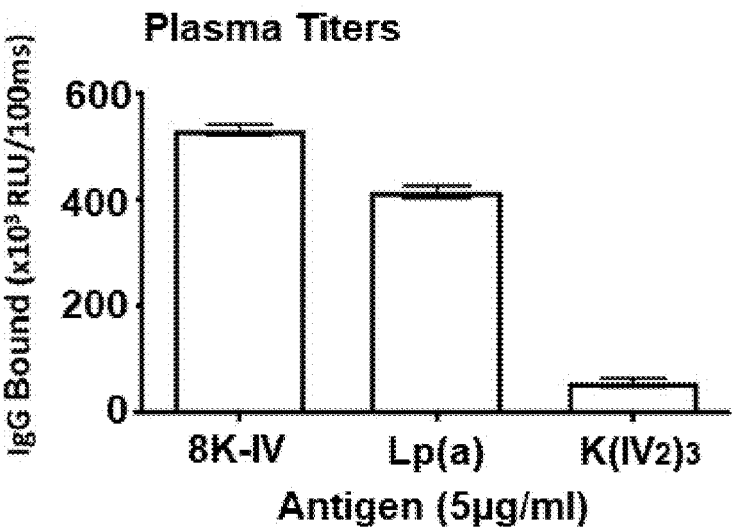
FIG. 2A-D shows the generation of isoform independent Lp(a) monoclonal antibody LPA-KIV9. (A) Mouse plasma titers of Lp(a)-specific antibodies: Following the first boost target-specific antibody titers were determined by ELISA against immobilized antigen by screening serial dilutions of the serum. The graph represents the mean of technical triplicates measurements at 1:400 plasma dilution. (B) Hybridoma screening: 576 hybridoma colonies were collected and expanded. Supernatants were screened by ELISA against the target antigen Lp(a) and counter-screened against antigen $K(IV_2)_3$. The graph shows a representative result of 8 colonies and multiple screening rounds. (C) Limiting dilution: To ensure monoclonality, 10 positive colonies were subjected to 2 cycles of limiting dilutions, using semi-solid gel without hypoxanthine-aminopterin-thymidine medium. Collected subclones were tested by ELISA. Colony #1 found to specifically binds Lp(a), but not to plasminogen and $KIV_2$. These two colonies were found to have identical CDR3 sequences in their heavy and light chains thus derived from the same clone. Colony 1 was tested 5 times and designated LPA-$KIV_9$. (D) Purified LPA-$KIV_9$ binding to Lp(a) (5 ug/ml) was tested by ELISA. The graph shows the mean of 2-4 technical replicates. Mean±SD.
Figure 2B:
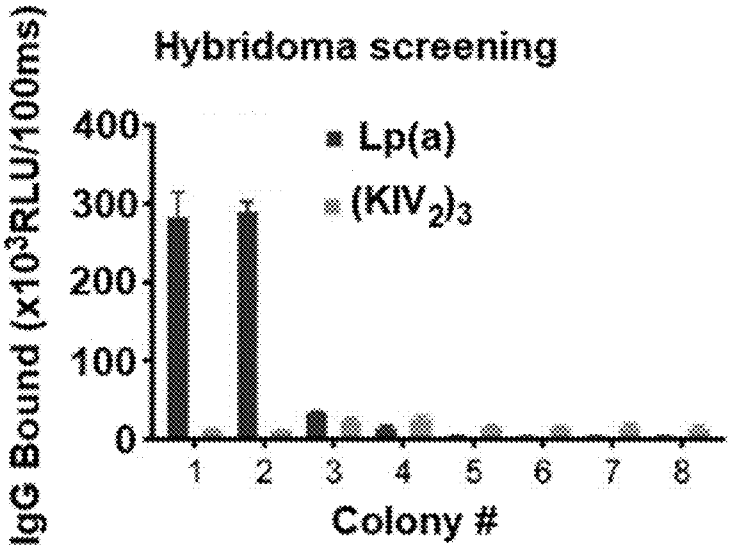
Figure 2C:
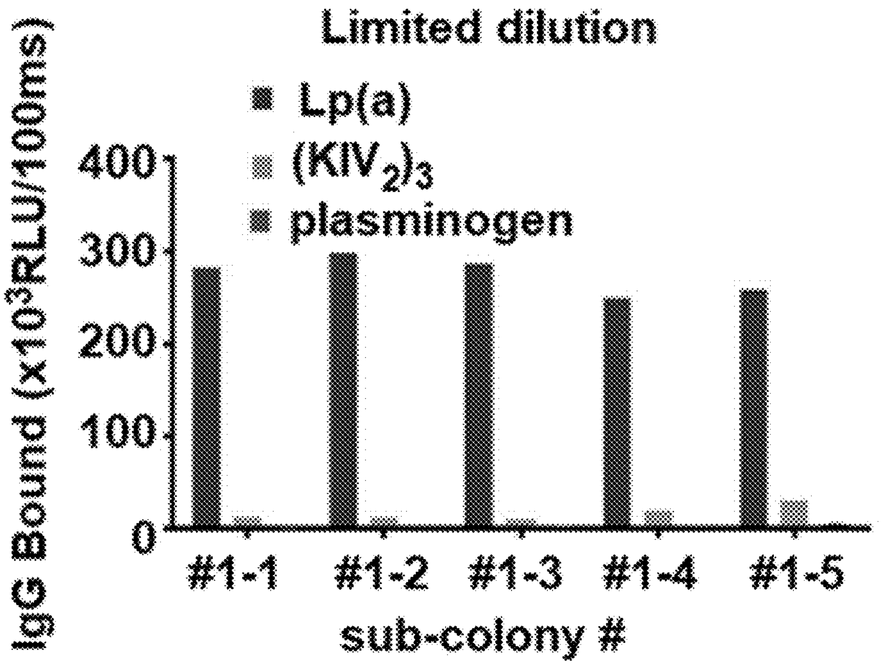
Figure 2D:
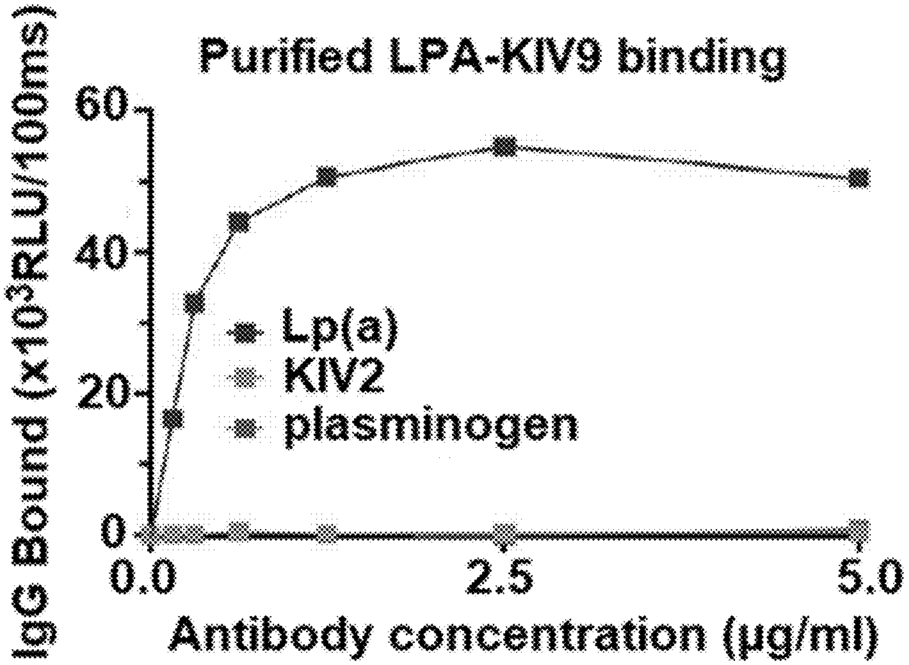

Generation and characterization of monoclonal antibodies. Following the immunization protocol using the 8K-IV apo(a) construct, mouse plasma was screened for the generation of IgG monoclonal antibodies binding Lp(a). Plasma contained strong binding to the 8K-IV construct and Lp(a), with background levels of binding to the $K(IV_2)_3$ construct (FIG. 2A). Hybridomas were then generated, 576 colonies were collected, expanded and screened by ELISA for production of IgG antibodies against Lp(a), resulting in 88 positive colonies that were expanded and re-tested. Two colonies were selected for their robust IgG binding to Lp(a) but not $K(IV_2)_3$ (FIG. 2B). Both colonies were subjected to two cycles of limiting dilution to ensure monoclonality. On further analysis, these were found to have identical CDR3 sequences in their heavy and light chains (Table A) and thus were derived from the same clone. All daughter clones were positive for binding to Lp(a) but not to $K(IV_2)_3$ or plasminogen (FIG. 2C). One colony was expanded in culture and the antibody LPA-$KIV_9$ was purified and shown to be an IgG1 isotype. Testing by direct ELISA of the purified LPA-$KIV_9$ showed a dose-dependent specific reactivity with Lp(a), with no cross-reactivity with $K(IV_2)_3$ or plasminogen (FIG. 2D)

TABLE A

LPA-KIV9 Heavy chain (IGHV1-15*01)(polynucleotide sequence = SEQ ID NO: 1; polypeptide sequence = SEQ ID NO: 2; CDR1 = SEQ ID NO: 3 (nucleic acid) and 4 (peptide); CDR2 = SEQ ID NO: 5(nucleic acid) and 6 (peptide); CDR3 = SEQ ID NO: 7(nucleic acid) and 8 (peptide))

```
ATGGAATGGAGCTGGGTCTTTCTCTTCCTCCTGTCAGTAACTGCAGGTGTCCAATCCCAGGTTCAATTGCAGCAGTCTGGG   81
 M  E  W  S  W  V  F  L  F  L  L  S  V  T  A  G  V  Q  S  Q  V  Q  L  Q  Q  S  G   27
            Signal peptide

GCTGAGCTGGTGAGGCCTGGGGCTTCAGTGAAACTGTCCTGCAAGGCTTTGGGCTACACATTTACTGACTATGAATTGCAC  162
 A  E  L  V  R  P  G  A  S  V  K  L  S  C  K  A  L  G  Y  T  F  T  D  Y  E  L  H   54
                                                            CDR1

TGGCTGAAGCAGACACCTGTGCATGGCCTGGAATGGATTGGAGCTGTTCATCCAGGAAGCGGTGGTTCTGCCTACAATCAG  243
 W  L  K  Q  T  P  V  H  G  L  E  W  I  G  A  V  H  P  G  S  G  G  S  A  Y  N  Q   81
                                                      CDR2

AACTTCAAGGACAAGGCCACACTGACTGCAGACAAATCCTCCAGCACAGCCTATATGGAGCTCAGCAGCCTGACATCTGAG  324
 N  F  K  D  K  A  T  L  T  A  D  K  S  S  S  T  A  Y  M  E  L  S  S  L  T  S  E  108

GACTCTGCTGTCTATTACTGTACAAGAGAAGGACCTTTCTACTGGGGCCAAGGCACCACTCTCACAGTCTCCTCA        399
 D  S  A  V  Y  Y  C  T  R  E  G  P  F  Y  W  G  Q  G  T  T  L  T  V  S  S        133
                         CDR3
```

TABLE B

LPA-KIV9 Light chain (IGKV1-110*01) (polynucleotide sequence = SEQ ID NO: 9; polypeptide sequence = SEQ ID NO: 10; CDR1 = SEQ ID NO: 11 and 12; CDR2 = SEQ ID NO: 13 and 14; CDR3 = SEQ ID NO: 15 and 16)

```
ATGAAGTTGCCTGTTAGGCTGTTGGTGCTGATGTTCTGGATTCCTGCTTCCAGTAGTGATGTTGTGATGACCCAAACTCCA   81
 M  K  L  P  V  R  L  L  V  L  M  F  W  I  P  A  S  S  S  D  V  V  M  T  Q  T  P   27
            Signal peptide

CTCTCCCTGCCTGTCAGTCTTGGAGATCAAGCCTCCATCTCTTGTAGATCTAGTCAGAGCCTTGTACACAGTAATGGAAAC  162
 L  S  L  P  V  S  L  G  D  Q  A  S  I  S  C  R  S  S  Q  S  L  V  H  S  N  G  N   54
                                                               CDR1

GCCTATTTACATTGGTACCTGCAGAAGCCAGGCCAGTCTCCAAAGCTCCTGATCTACAAAGTTTCCAACCGATTTTCTGGG  243
 A  Y  L  H  W  Y  L  Q  K  P  G  Q  S  P  K  L  L  I  Y  K  V  S  N  R  F  S  G   81
                                                         CDR2

GTCCCAGACAGGTTCAGTGGCAGTGGATCAGGGACAAATTTCACACTCAAGATCAGTAGAGTGGAGGCTGAGGATCTGGGA  324
 V  P  D  R  F  S  G  S  G  S  G  T  N  F  T  L  K  I  S  R  V  E  A  E  D  L  G  108

ATTTATTTCTGCTCTCAAAGTACACATGTTCCGCTCACGTTCGGTGCTGGGACCAAGCTGGAGCTGAAA              393
 I  Y  F  C  S  Q  S  T  H  V  P  L  T  F  G  A  G  T  K  L  E  L  K              131
                   CDR3
```

Figure 3A:
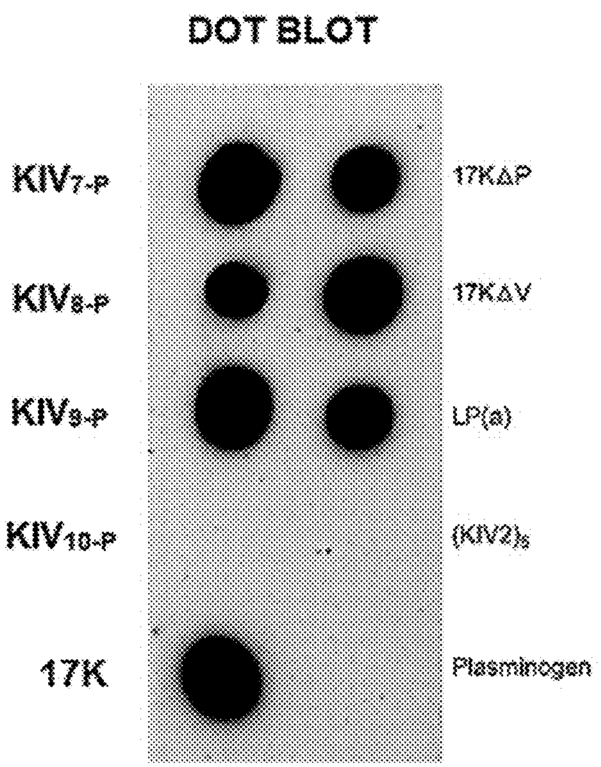
FIG. 3A-B shows identification of the LPA-$KIV_9$ epitope on apolipoprotein(a). Lp(a) and array of recombinant apo(a) constructs were used to test LPA-$KIV_9$ binding by (A) Dot-blot (25 ng protein/dot) and (B) western blot (WB) under reducing conditions (250 ng protein/well). LPA-$KIV_9$ demonstrated a lack of reactivity with plasminogen or $KIV_2$, and high immunoreactivity with Lp(a) and all apolipoprotein (a) constructs containing $KIV_9$.
Figure 3B:
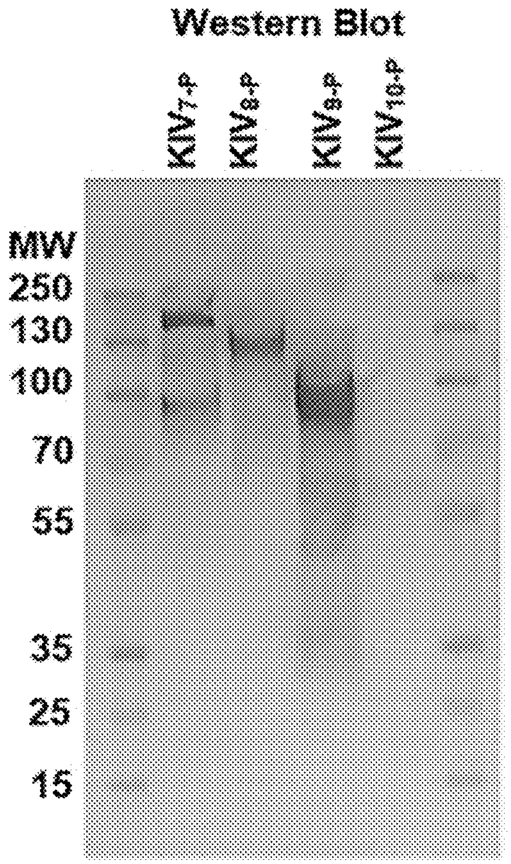

Determination of the binding domain of LPA-KIV$_9$ on apolipoprotein (a). To determine the site on apolipoprotein (a) to which LPA-KIV$_9$ bound, binding was tested to an array of apolipoprotein(a) recombinant constructs by dot-blot (FIG. 3A) and Western blot (FIG. 3B). By dot-blot, LPA-KIV$_9$ reacted with all tested constructs containing various numbers of kringle segments including KIV6-P, KIV7-P, KIV8-P, KIV9-P containing sequence from KIV6, KIV7, KIV8 and KIV9 to the end of the protease domain, respectively. It also recognized the 17K full-length human construct, the 17KdeltaV construct missing KV and the 17KdeltaP construct missing the protease-like domain (FIG. 3A). However, LPA-KIV9 did not react with KIV$_{10\text{-}P}$ and K(IV$_2$)$_5$ (i.e., the only construct not containing KIV9) consistent with the epitope being present on KIV$_9$. The specific binding pattern was duplicated with western blotting showing that the presence of KIV9 was required for LPA-KIV9 immunoreactivity (FIG. 3B).

Figure 4A:
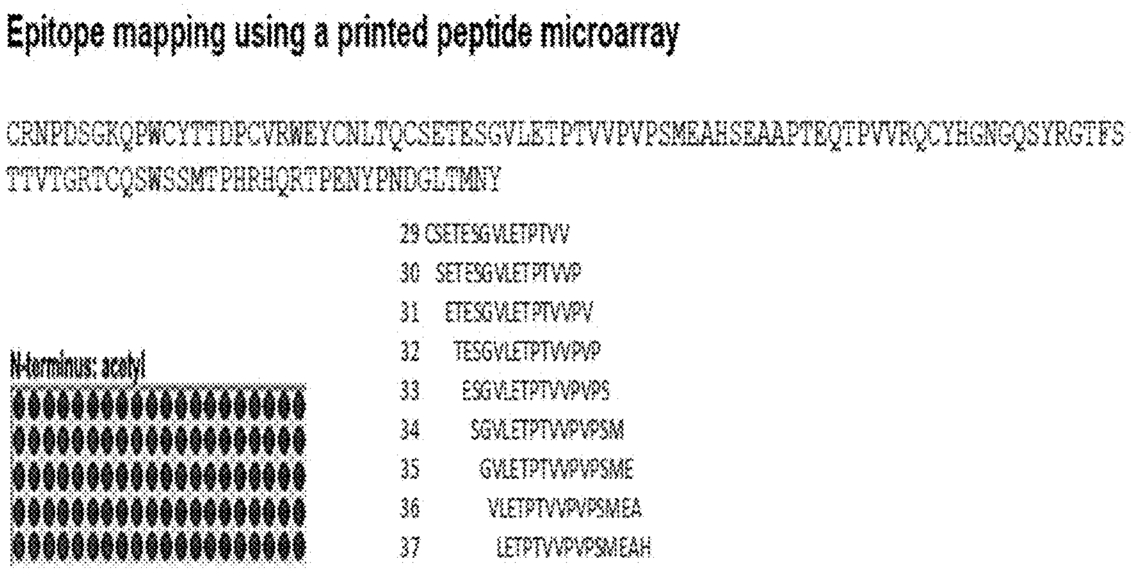

Determination of the peptide sequence on the epitope recognized by LPA-KIV$_9$. A peptide library spanning KIV$_9$ consisting of 100 overlapping peptides, each 15 amino acids in length, was designed (FIG. 4A). Antibody LPA-KIV$_9$ bound to 9 overlapping peptide fragments on KIV$_9$ (FIG. 4B), which comprised the 23 amino acid epitope CSETESGVLETPTVVPVPSMEAH (SEQ ID NO:18). This epitope is 11 amino acids downstream of cysteine 4057 on apolipoprotein(a) (shown in pink in FIG. 4C) that creates the disulfide bond with cysteine 4236 of apoB-100. The three-dimensional structure of the epitope on apolipoprotein(a) was predicted by a Swiss-model server, showing the epitope is a loop surface epitope toward the C-terminal end of KIV$_9$ and 3 amino acids away from KIV$_{10}$ (shown in green, FIG. 4C).

Application of LPA-KIV$_9$ to the measurement of plasma Lp(a) levels. Lp(a) was measured as "true Lp(a)" or "total apo(a)" molar concentration in 100 subjects with randomly distributed Lp(a) levels using two established in-house chemiluminescent ELISAs and two novel ELISAs with LPA-$KIV_9$ using parallel methodology. Table 1 displays the descriptive statistics, showing median levels among assays ranged from 16.4-19.7 nmol/L, respectively, and absolute levels ranged from 0-314.1 nmol/L.

TABLE 1

Descriptive statistics of the Lp (a) values (in nmol/L) of the four Lp (a) enzyme-linked immunoassays:

| | b-LPA4/MB47 | b-LPA4/LPA4 | b-LPA-$KIV_9$/MB47 | b-LPA-$KIV_9$/LPA4 |
|---|---|---|---|---|
| N | 100 | 100 | 100 | 100 |
| Median | 19.7 | 16.4 | 18.6 | 16.4 |
| Interquartile range | (6.9-72.5) | (6.8-48.7) | (10.3-60.0) | (4.3-59.1) |
| Range | 0.1-227.2 | 1.7-193.6 | 0.0-189.1 | 0.0-314.1 |

b-LPA4/MB47 represents capture apoB-100 with MB47 and detect with biotin-LPA4, b-LPA4/LPA4 represents capture apolipoprotein (a) with LPA4 and detect with biotin-LPA4, b-LPA-$KIV_9$/MB47 represents capture apoB-100 with MB47 and detect with biotin-LPA-$KIV_9$ and b-LPA-$KIV_9$/LPA4 represents capture apolipoprotein (a) with LPA4 and detect with biotin-LPA-$KIV_9$.

Comparing assays with similar capture/detection antibody formats, significant correlations were present between true Lp(a) assays (b-LPA4/BM47 versus b-LPA-$KIV_9$/MB47, r=0.85, p<0.001) and total apo(a) assays (b-LPA4/LPA4 versus b-LPA-$KIV_9$/LPA4 (r=0.94, p<0.001). Additionally, significant correlations were present between true Lp(a) and "total apo(a)" (Table 2).

TABLE 2

Spearman correlation matrix (r and p-values) of various true Lp (a)/total apo (a) assays:

| Assay | b-LPA4/LPA4 | b-LPA-$KIV_9$/MB47 | b-LPA-$KIV_9$/LPA4 |
|---|---|---|---|
| b-LPA4/MB47 | 0.941 (p < 0.001) | 0.850 (p < 0.001) | 0.894 (p < 0.001) |
| b-LPA4/LPA4 | | 0.906 (p < 0.001) | 0.939 (p < 0.001) |
| b-LPA-$KIV_9$/MB47 | | | 0.953 (p < 0.001) |

Figures 5A, 5B, 5C:
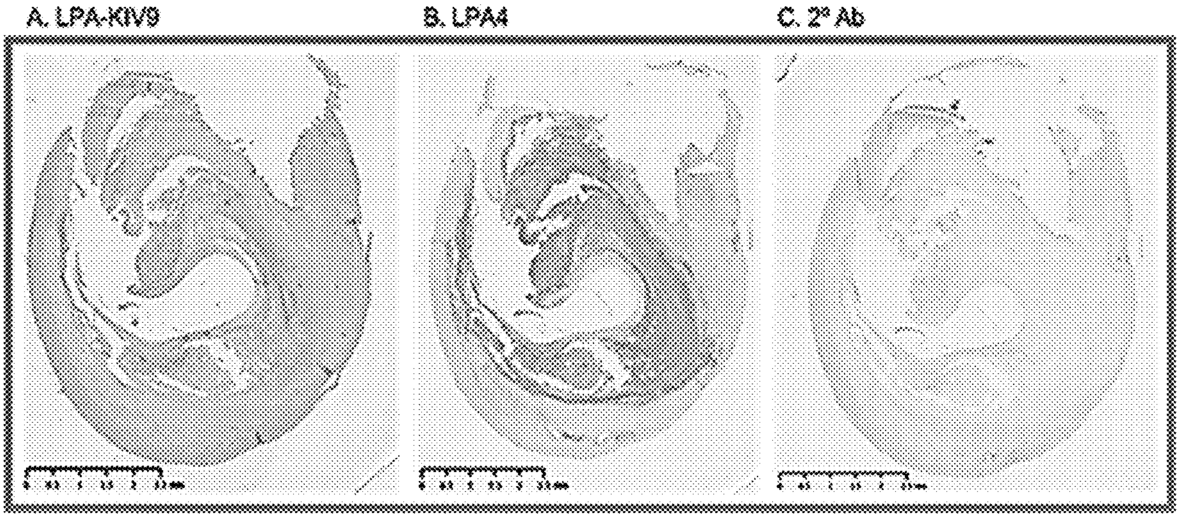
FIG. 5A-C shows LPA-KIV9 epitopes in human atherosclerotic lesions. Consecutive cross-sections of human carotid endarterectomy specimens were stained with monoclonal antibodies LPA-KIV9 (A), LPA4 (B) and with no primary antibody but with the secondary antibody only (C). Representative images of three specimens tested.

Immunohistochemistry. Human carotid endarterectomy specimens removed en bloc (with plaque only and no media/adventitia) were stained with LPA-KIV9 and for comparison monoclonal antibody LPA4. Both antibodies had similar staining patterns, primarily detecting the center of the atheroma, with less staining toward the deep medial areas (FIG. 5). No staining was noted in absence of primary antibodies.

A number of embodiments have been described herein. Nevertheless, it will be understood that various modifications may be made without departing from the spirit and scope of this disclosure. Accordingly, other embodiments are within the scope of the following claims.

What is claimed is:

1. An antibody or antibody fragment that recognizes and binds to lipoprotein(a), wherein the antibody or antibody fragment comprises a variable heavy chain ($V_H$) domain and/or a variable light chain ($V_L$) domain, and wherein (a) the $V_H$ domain comprises an amino acid sequence that includes complementarity determining regions (CDRs) of: SEQ ID NO:4; SEQ ID NO:6; and SEQ ID NO:8; and (b) the $V_L$ domain comprises an amino acid sequence that includes complementarity determining regions (CDRs) of: SEQ ID NO:12; KVS; and SEQ ID NO: 15.

2. The antibody or antibody fragment of claim 1, wherein the $V_H$ domain comprises an amino acid sequence of SEQ ID NO:2, and/or the $V_L$ domain comprises an amino acid sequence of SEQ ID NO:10.

3. The antibody or antibody fragment of claim 1, wherein the heavy and light chain domains are linked to an Fc region.

4. An antibody fragment of claim 1 comprising a single chain variable fragment ("scFv") that recognizes an epitope of KIV9 of lipoprotein(a).

5. The scFv of claim 4, wherein the scFv is soluble under physiological conditions.

6. The scFv of claim 4, wherein the scFv comprises a light-chain variable region having a sequence that is at least 95% identical to the sequence as set forth in SEQ ID NO:10.

7. The scFv of claim 6, wherein the scFv comprises a heavy chain variable region having a sequence that is at least 95% identical to the sequence as set forth in SEQ ID NO:2.

8. The antibody or antibody fragment of claim 1, wherein the antibody is chimeric.

9. A pharmaceutical composition comprising an antibody of claim 8 and a carrier, excipient, or stabilizer.

10. An antibody or antibody fragment of claim 1 bound to a solid substrate.

11. An antibody or antibody fragment of claim 1 operably linked to a detectable label.

12. A polynucleotide that encodes an antibody or antibody fragment of claim 1.

13. The polynucleotide of claim 12, wherein the polynucleotide (i) comprises a sequence that hybridizes to a nucleic acid consisting of SEQ ID NO:1 and/or 9 and encodes an antibody that binds to KIV9 of Lp(a); or (ii) comprises a sequence that encodes a polypeptide having a sequence of SEQ ID NO:2 and/or 10.

14. A vector comprising a polynucleotide of claim 13.

15. A host cell transformed with the polynucleotide of claim 13.

16. A chimeric antigen receptor comprising a binding domain containing the VH and/or VL domains of claim 1.

17. A CAR-T cell comprising the chimeric antigen receptor of claim 16.

* * * * *